US012575806B2

(12) United States Patent
Viswanath et al.

(10) Patent No.: US 12,575,806 B2
(45) Date of Patent: Mar. 17, 2026

(54) POWER REDUCTION OF FETAL ULTRASOUND TRANSDUCERS FOR EXTENDED BATTERY LIFE

(71) Applicant: GE Precision Healthcare LLC, Waukesha, WI (US)

(72) Inventors: Shrihari Viswanath, Bangalore (IN); Rajendra Naik, Bangalore (IN); Benoy Abraham, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/426,572

(22) Filed: Jan. 30, 2024

(65) Prior Publication Data

US 2025/0241616 A1    Jul. 31, 2025

(51) Int. Cl.
*A61B 8/08*      (2006.01)
*A61B 8/00*      (2006.01)
*A61B 8/02*      (2006.01)

(52) U.S. Cl.
CPC .............. *A61B 8/0866* (2013.01); *A61B 8/02* (2013.01); *A61B 8/4483* (2013.01); *A61B 8/488* (2013.01); *A61B 8/56* (2013.01)

(58) Field of Classification Search
CPC ....... A61B 8/0866; A61B 8/02; A61B 8/4483; A61B 8/488; A61B 8/56
See application file for complete search history.

(56) References Cited

U.S. PATENT DOCUMENTS 5,088,497 A    2/1992   Ikeda
5,528,168 A  *  6/1996   Kleveland ............ H03K 3/0233
                                                326/86

(Continued)

FOREIGN PATENT DOCUMENTS

CN      105342640  B      2/2016
CN      105913355  A      8/2016
              (Continued)

OTHER PUBLICATIONS

EP application 25150798.4 filed Jan. 8, 2025—extended Search Report issued Jun. 16, 2025; 8 pages.

(Continued)

*Primary Examiner* — Sanjay Cattungal

(74) *Attorney, Agent, or Firm* — Amin, Turocy & Watson, LLP

(57)                    ABSTRACT

Techniques for reducing power consumption by fetal ultrasound transducers are provided. In an example, a fetal sensor device (FSD) comprising a processor, controls operations an ultrasound transducer of the FSD in accordance with a power optimization protocol that results in minimizing power consumption by the FSD, wherein the ultrasound transducer is configured to measure one or more fetal parameters of a fetus using doppler based ultrasound technology, wherein the FSD operates in an active mode that comprises alternating between transmit periods wherein the ultrasound transducer transmits ultrasound signals, and receive periods wherein the ultrasound transducer measures reflected signals of the ultrasound signals that are received by the ultrasound transducer during the receive periods, and wherein the controlling comprises controlling a transmission power of the ultrasound signals and/or a duration of the transmit periods during the active mode in accordance with the power optimization protocol.

24 Claims, 14 Drawing Sheets

(56) References Cited

U.S. PATENT DOCUMENTS

| | | | |
|---|---|---|---|
| 6,288,577 B1 * | 9/2001 | Wong | H03K 5/24 |
| | | | 326/14 |
| 6,320,406 B1 * | 11/2001 | Morgan | H04L 25/08 |
| | | | 326/14 |
| 6,650,149 B1 * | 11/2003 | Wong | H03K 19/007 |
| | | | 327/14 |
| 6,862,432 B1 | 3/2005 | Kim | |
| 6,963,249 B2 | 11/2005 | Devries et al. | |
| 7,292,119 B2 | 11/2007 | Urakawa | |
| 7,949,444 B2 | 5/2011 | Mukherjee | |
| 7,983,626 B2 | 7/2011 | Kim | |
| 8,055,887 B2 | 11/2011 | Karstens | |
| 8,407,158 B2 | 3/2013 | Suri et al. | |
| 8,696,578 B2 * | 4/2014 | Kabakov | A61B 8/40 |
| | | | 600/453 |
| 8,738,663 B2 | 5/2014 | Gonzalez et al. | |
| 8,746,548 B2 | 6/2014 | Terwilliger et al. | |
| 9,183,603 B2 | 11/2015 | Borges et al. | |
| 9,396,037 B2 | 7/2016 | Morsi et al. | |
| 9,536,044 B2 | 1/2017 | White et al. | |
| 9,672,458 B2 | 6/2017 | Burkhart et al. | |
| 9,734,448 B2 | 8/2017 | Bolich | |
| 10,025,791 B2 | 7/2018 | Lee | |
| 10,402,781 B2 | 9/2019 | Terwilliger et al. | |
| 10,638,999 B2 | 5/2020 | Shah | |
| 10,789,264 B2 | 9/2020 | Crabtree et al. | |
| 10,810,390 B2 | 10/2020 | Hegendoerfer et al. | |
| 10,901,834 B2 | 1/2021 | Abhinav et al. | |
| 10,902,232 B2 | 1/2021 | Peng | |
| 10,949,440 B2 | 3/2021 | Schoueri et al. | |
| 11,087,878 B2 | 8/2021 | Vesto et al. | |
| 11,240,181 B1 | 2/2022 | Nagaraja et al. | |
| 11,309,060 B2 | 4/2022 | Janevski et al. | |
| 11,321,338 B2 | 5/2022 | Okorafor et al. | |
| 11,327,989 B2 | 5/2022 | Wu et al. | |
| 11,451,201 B1 | 9/2022 | Hoffman et al. | |
| 11,481,738 B2 | 10/2022 | Tong et al. | |
| 11,599,729 B2 | 3/2023 | Wu | |
| 11,842,188 B2 | 12/2023 | Bregman et al. | |
| 2004/0036538 A1 | 2/2004 | Devries et al. | |
| 2004/0090265 A1 * | 5/2004 | Pradhan | H03F 3/68 |
| | | | 330/69 |
| 2005/0130699 A1 | 6/2005 | Kim | |
| 2005/0134491 A1 | 6/2005 | Huang et al. | |
| 2005/0219003 A1 | 10/2005 | Urakawa | |
| 2007/0243834 A1 | 10/2007 | Takei | |
| 2007/0260155 A1 | 11/2007 | Rapoport et al. | |
| 2009/0043203 A1 | 2/2009 | Pelissier et al. | |
| 2010/0168596 A1 * | 7/2010 | Jaeschke | A61B 8/5276 |
| | | | 600/511 |
| 2010/0191117 A1 | 7/2010 | Kabakov | |
| 2010/0274145 A1 * | 10/2010 | Tupin, Jr. | A61B 5/0022 |
| | | | 600/511 |
| 2010/0274750 A1 | 10/2010 | Oltean et al. | |
| 2011/0254567 A1 | 10/2011 | Gehrig et al. | |
| 2011/0295102 A1 | 12/2011 | Lakkis et al. | |
| 2012/0053465 A1 * | 3/2012 | Kudoh | A61B 8/4254 |
| | | | 600/443 |
| 2012/0123267 A1 | 5/2012 | Dow et al. | |
| 2012/0232398 A1 | 9/2012 | Roham et al. | |
| 2012/0286889 A1 | 11/2012 | Park et al. | |
| 2013/0087609 A1 | 4/2013 | Nichol et al. | |
| 2013/0123637 A1 * | 5/2013 | Wohlschlager | A61B 8/02 |
| | | | 600/453 |
| 2013/0158407 A1 * | 6/2013 | Kabakov | A61B 8/0866 |
| | | | 600/453 |
| 2013/0245436 A1 * | 9/2013 | Tupin, Jr. | A61B 5/6833 |
| | | | 600/430 |
| 2014/0163378 A1 * | 6/2014 | Ohshima | A61B 8/5207 |
| | | | 600/447 |
| 2014/0276070 A1 * | 9/2014 | Kabakov | A61B 8/0883 |
| | | | 600/453 |
| 2015/0146772 A1 * | 5/2015 | Fujimori | H04L 1/0002 |
| | | | 375/238 |

| | | | |
|---|---|---|---|
| 2015/0219580 A1 | 8/2015 | Gehrig et al. | |
| 2015/0302176 A1 | 10/2015 | Lyons et al. | |
| 2015/0372664 A1 | 12/2015 | Walker et al. | |
| 2016/0204765 A1 | 7/2016 | Ferriss et al. | |
| 2017/0043189 A1 | 2/2017 | Stoddard et al. | |
| 2017/0071579 A1 * | 3/2017 | Ko | A61B 8/546 |
| 2017/0303899 A1 | 10/2017 | Willsie | |
| 2018/0115197 A1 | 4/2018 | Li et al. | |
| 2018/0338746 A1 * | 11/2018 | Wu | A61B 8/54 |
| 2019/0019090 A1 | 1/2019 | Chacko et al. | |
| 2019/0370671 A1 | 12/2019 | Canedo et al. | |
| 2020/0365262 A1 | 11/2020 | Sreenivasan et al. | |
| 2020/0380076 A1 | 12/2020 | Taylor | |
| 2021/0064932 A1 | 3/2021 | Wang et al. | |
| 2021/0241897 A1 | 8/2021 | Casse et al. | |
| 2022/0005083 A1 | 1/2022 | Patterson et al. | |
| 2022/0189618 A1 | 6/2022 | Klassen et al. | |
| 2022/0233174 A1 | 7/2022 | Hwang | |
| 2022/0293246 A1 | 9/2022 | Tweedie et al. | |
| 2022/0337189 A1 | 10/2022 | Huang et al. | |
| 2022/0374300 A1 | 11/2022 | Che et al. | |
| 2023/0034748 A1 | 2/2023 | Bull et al. | |
| 2023/0168895 A1 | 6/2023 | Shah et al. | |
| 2023/0238103 A1 | 7/2023 | Murphy et al. | |
| 2023/0259821 A1 | 8/2023 | Travalini et al. | |
| 2023/0335236 A1 | 10/2023 | Dambman et al. | |
| 2023/0335238 A1 | 10/2023 | Danckwardt | |
| 2023/0338000 A1 | 10/2023 | Kiran | |
| 2024/0296352 A1 | 9/2024 | Yanosy, Jr. et al. | |
| 2025/0241615 A1 | 7/2025 | Naik et al. | |

FOREIGN PATENT DOCUMENTS

| | | |
|---|---|---|
| CN | 108231145 A | 6/2018 |
| CN | 110035303 A | 7/2019 |
| CN | 111899852 A | 11/2020 |
| CN | 112364148 A | 2/2021 |
| CN | 114073546 A | 2/2022 |
| CN | 114118062 A | 3/2022 |
| CN | 114882979 A | 8/2022 |
| CN | 114898848 A | 8/2022 |
| CN | 115098673 A | 9/2022 |
| CN | 115964460 A | 4/2023 |
| CN | 114446423 A | 6/2023 |
| WO | 2020/167316 A1 | 8/2020 |
| WO | 2022206822 A1 | 10/2022 |
| WO | 2022/229088 A1 | 11/2022 |
| WO | 2023/088983 A1 | 5/2023 |

OTHER PUBLICATIONS

Non-Final office action received for U.S. Appl. No. 18/422,591 dated Dec. 20, 2024, 42 pages.

Deloitte, "Tech Trends 2021", Deloitte Insights, https://www2.deloitte.com/content/dam/insights/articles/7023_TT-machine-data-revolution-feeding-the-machine/DI_2021-TT-machine-data-revolution.pdf, last accessed Nov. 2, 2023, 21 pages.

Anadiotis, George, "5 Technology Trends for the Roaring 20s, Part 2: AI, Knowledge Graphs, Infinity and Beyond", On-line publication on ZD NET, https://www.zdnet.com/article/5-technology-trends-for-the-roaring-20s-part-2-aiknowledge-graphs-infinity-and-beyond/, Jan. 16, 2020, 9 pages.

McMahan et al., "Federated Learning: Collaborative Machine Learning without Centralized Training Data", Google Blog, https://ai.googleblog.com/2017/04/federated-learning-collaborative.html, Apr. 6, 2017, 5 pages.

TensorFlow, "TensorFlow Federated: Machine Learning on Decentralized Data", Online Available at URL: https://www.tensorflow.org/federated, last accessed Aug. 28, 2023, 4 pages.

Schema.org, Company website https://schema.org/, last accessed Aug. 28, 2023, 1 page.

Schema.org, "IoT and Schema.org: Getting Started", https://schema.org/docs/iot-gettingstarted.html, last accessed Sep. 19, 2023, 15 pages.

Maguire et al., "A Metadata-Based Architecture for User-Centered Data Accountability", Electron Markets, Online available at https://

(56)          References Cited

OTHER PUBLICATIONS link.springer.com/article/10.1007/s12525-015-0184-z, vol. 25, 2015, pp. 155-160.
Chavarukattil, et al. "Generative Artificial Intelligence Driven Self-healing Agent for Medical Devices" U.S. Appl. No. 18/749,679, filed Jun. 21, 2024, 37 pages.
Anonymously, "Dual Ultrasound Switching Using Analog Switches", IPCOM000239085D, Oct. 10, 2014, 5 pages.
Docker, M. F., "Doppler Ultrasound Monitoring Technology", British Journal of Obstetrics and Gynaecology, vol. 100, No. 9, Mar. 1993, pp. 18-20.
Extended European Search Report received for European Patent Application Serial No. 25150797.6 dated Jun. 2, 2025, 11 pages.
Non Final Office action received for U.S. Appl. No. 18/426,977 dated Sep. 17, 2025, 21 pages.
Anonymously, "Direct Digital Synthesis Based Ultrasound Doppler Transducer", IP.com, IP.com Inc., IPCOM000224998D, Jan. 18, 2013, 10 pages.
Extended European Search Report received for European Patent Application Serial No. 2025, 14 pages.

* cited by examiner

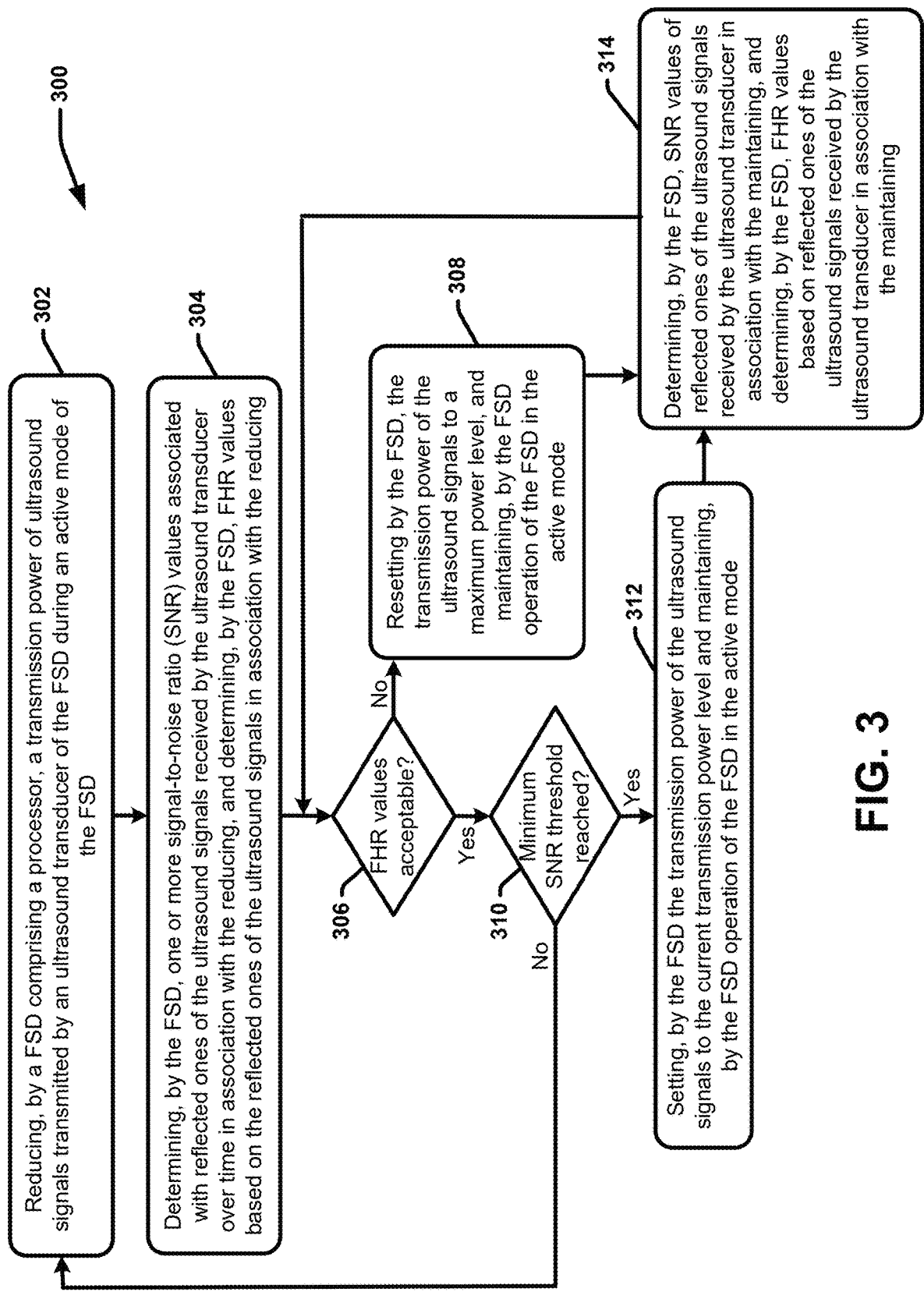

300

302 Reducing, by a FSD comprising a processor, a transmission power of ultrasound signals transmitted by an ultrasound transducer of the FSD during an active mode of the FSD 304 Determining, by the FSD, one or more signal-to-noise ratio (SNR) values associated with reflected ones of the ultrasound signals received by the ultrasound transducer over time in association with the reducing, and determining, by the FSD, FHR values based on the reflected ones of the ultrasound signals in association with the reducing 306 FHR values acceptable?

308 Resetting by the FSD, the transmission power of the ultrasound signals to a maximum power level, and maintaining, by the FSD operation of the FSD in the active mode 310 Minimum SNR threshold reached?

312 Setting, by the FSD the transmission power of the ultrasound signals to the current transmission power level and maintaining, by the FSD operation of the FSD in the active mode 314 Determining, by the FSD, SNR values of reflected ones of the ultrasound signals received by the ultrasound transducer in association with the maintaining, and determining, by the FSD, FHR values based on reflected ones of the ultrasound signals received by the ultrasound transducer in association with the maintaining

Controlling, by a fetal sensor device (FSD) comprising a processor, operations of an ultrasound transducer of the FSD in accordance with a power optimization protocol that results in minimizing power consumption by the FSD, wherein the ultrasound transducer configured to measure signals representative of one or more fetal parameters of a fetus using doppler based ultrasound technology in association with positioning of the FSD on an external body of a mother of the fetus, wherein the FSD operates in an active mode that comprises alternating between transmit periods wherein the ultrasound transducer transmits ultrasound signals, and receive periods wherein the ultrasound transducer measures reflected ones of the ultrasound signals that are received by the ultrasound transducer during the receive periods, and wherein the controlling comprises controlling at least one of a transmission power of the ultrasound signals or a duration of the transmit periods during the active mode in accordance with the power optimization protocol.

FIG. 8

900

Activating, by a FSD comprising a processor, an active mode of the FSD, wherein the active mode comprises alternating between transmit periods wherein an ultrasound transducer of the FSD transmits ultrasound signals, and receive periods wherein the ultrasound transducer measures reflected signals of the ultrasound signals that are received by the ultrasound transducer during the receive periods

902

Adjusting by the FSD, a duration of the transmit periods during the active mode based on one or more SNR values of the reflected signals of the ultrasound signals and/or a depth of the fetus in accordance with a power optimization component that facilities minimizing power consumption by the FSD

1000

Activating, by a FSD comprising a processor, an active mode of the FSD, wherein the active mode comprises alternating between transmit periods wherein an ultrasound transducer of the FSD transmits ultrasound signals, and receive periods wherein the ultrasound transducer measures reflected signals of the ultrasound signals that are received by the ultrasound transducer during the receive periods, and wherein the transmit periods are constrained by a fixed duration defined by a start time and an end time

1002

Adjusting by the FSD, a duration and/or position of an active portion of the transmit periods in association with configuring the ultrasound transducer to only transmits the ultrasound signals during the active portion

1004

Monitoring, by the FSD, changes to a signal to noise ratio (SNR) associated with the reflected signals of the ultrasound signals in association with the adjusting

1006

Estimating, by the FSD, a depth of a heart of the fetus based on the changes in association with the adjusting

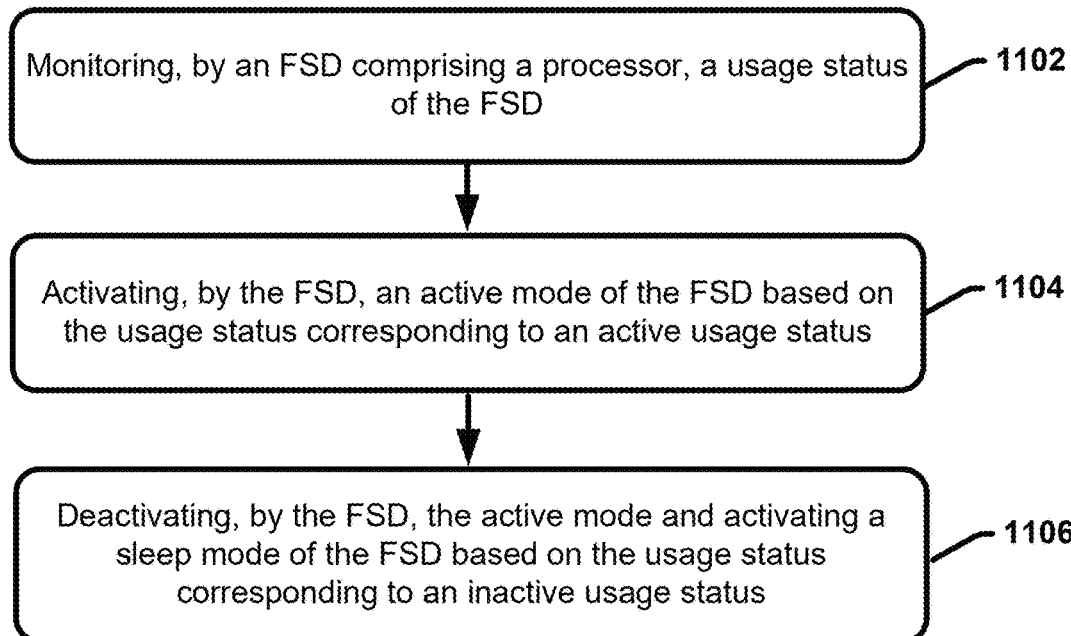
Monitoring, by an FSD comprising a processor, a usage status of the FSD　　1102
Activating, by the FSD, an active mode of the FSD based on the usage status corresponding to an active usage status　　1104
Deactivating, by the FSD, the active mode and activating a sleep mode of the FSD based on the usage status corresponding to an inactive usage status　　1106
FIG. 11

POWER REDUCTION OF FETAL ULTRASOUND TRANSDUCERS FOR EXTENDED BATTERY LIFE

TECHNICAL FIELD

This application relates to doppler ultrasound based fetal monitoring systems, and more particularly to techniques for reducing power consumption by fetal ultrasound transducers for extended battery life.

BACKGROUND

Fetal heart rate (FHR) monitoring is a routine procedure during pregnancy check-ups and labor to ensure the baby's health. It helps detect changes in FHR that may indicate distress or other issues, prompting appropriate medical intervention if necessary.

A doppler-based FHR monitoring system is a non-invasive FHR monitoring system that utilizes the Doppler effect to detect changes in as well as the absolute value of the FHR. The Doppler effect is a change in frequency or wavelength of a wave (in this case, ultrasound waves) when the source of the wave and the observer are in relative motion. In the context of FHR monitoring, the Doppler effect is used to detect and measure the heartbeat. A fetal sensor device (FSD) with an ultrasound transducer is placed on the mother's abdomen. The transducer emits sound waves (ultrasound waves) that travel through the mother's tissues and into the uterus. When these ultrasound waves encounter the fetal heart, they are reflected back toward the transducer. Due to the motion of the fetal heart (which beats rhythmically), the frequency of the reflected waves is slightly shifted (Doppler shift) compared to the emitted waves. The Doppler-based monitoring system detects these shifts and calculates the fetal heart rate (FHR) based on the repetitive frequency changes. The results are displayed on a monitor device or printed on a chart, allowing healthcare providers to assess the fetal heart rate and its variability.

Conventional doppler-based FHR monitoring systems utilize wired communication between the FSD and the monitor device. Wireless doppler-based FHR systems have been developed to provide greater mobility and convenience compared to traditional wired FHR systems. What sets a wireless FSD apart is its ability to transmit the FHR data wirelessly to the monitor device, thus eliminating physical wires or cables for connecting the FSD to the monitoring device.

While wireless FSDs offer numerous benefits, they also introduce new issues and challenges. One issue with wireless FSDs is power consumption. In particular, wireless FSDs rely on batteries for power and prolonged monitoring sessions, especially during extended labor, can drain the batteries, potentially leading to interruptions in monitoring Accordingly, techniques for minimizing power consumption while optimizing system performance are desired.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described that facilitate reducing power consumption by fetal ultrasound transducers for extended battery life.

According to an embodiment, a fetal sensor device (FSD) is provided that comprises an ultrasound transducer configured to measure signals representative of one or more fetal parameters of a fetus using doppler based ultrasound technology in association with positioning of the FSD on an external body of a mother of the fetus, wherein the FSD operates in an active mode that comprises alternating between transmit periods wherein the ultrasound transducer transmits ultrasound signals, and receive periods wherein the ultrasound transducer measures reflected signals of the ultrasound signals that are received by the ultrasound transducer during the receive periods. The FSD further comprises at least one memory that stores computer-executable components, and at least one processor that executes the computer-executable components stored in the at least one memory, wherein the computer-executable components comprise a control component that controls at least one of a transmission power of the ultrasound signals or a duration of the transmit periods during the active mode in accordance with a power optimization protocol that results in minimizing power consumption by the ultrasound transducer. In various embodiments, the FSD comprises or corresponds to a wireless FSD. For example, the FSD can comprise an onboard power source from which the ultrasound transducer consumers power and a communication component that wirelessly communicates information between the FSD and a monitor device.

In various implementations, the control component adjusts the transmission power during the active mode based on a signal-to-noise (SNR) ratio of the reflected signals of the ultrasound signals. For example, the control component can incrementally decrease the transmission power during the active mode until the reflected signals of the ultrasound signals achieve a minimum SNR. More particularly, the one or more fetal parameters can comprise a heart rate of the fetus, and wherein the computer-executable components further comprise a signal processing component that determines values of the heart rate based on the reflected signals of the ultrasound signals, and wherein the control component incrementally decreases the transmission power based on the values corresponding to a valid fetal heart value, and wherein the control component increases the transmission power during based on one or more of the values corresponding to an invalid value.

Additionally, or alternatively, the control component adjusts the duration of the transmit periods during the active mode based on a depth of the heart of the fetus within the womb. In some implementations, the computer executable components further comprise a depth estimation component that estimates the depth of the heart based on the reflected signals of the ultrasound signals in association with incrementally decreasing the duration of the transmit periods by the control component and based on based on a signal to noise (SNR) ratio of the reflected signals of the ultrasound signals being a same value or within a same value range in association with the adjusting, and wherein the control component sets the duration of the transmit periods based on the depth.

In various embodiments, the transmit periods are constrained by a first duration defined by a start time and end time, wherein the duration of the transmit periods controlled by the control component correspond to a second duration within the first duration, wherein the ultrasound transducer only transmits the ultrasound signals during the second duration, and wherein the control component further adjusts a position of the second duration relative to the start time and the end time in accordance with the power optimization protocol. In some implementations of these embodiments, the control component adjusts the position of the second duration based on a depth of the heart of the fetus within the womb. In some implementations of these embodiments, the computer executable components further comprise a depth estimation component that estimates a depth of a heart of the fetus based on the reflected signals of the ultrasound signals in association with adjusting the position of the second duration by the control component and based on a SNR of the reflected signals of the ultrasound signals being a same value or within a same value range in association with the adjusting, and wherein the control component sets the position of the second duration based on the depth. In other implementations of these embodiments, the control component monitors a SNR of the reflected signals of the ultrasound signals and adjust the position of the second duration by moving the position of the second duration towards the start time based on a decrease to the SNR and moving the position of the second away from the start time based on increase to the SNR. With these implementations, the computer executable components can further comprise a depth estimation component that estimates and tracks changes to a depth of the heart of the fetus within the womb based in association with moving the position of the second duration.

In other implementations, the control component monitors a SNR of the reflected signals of the ultrasound signals and decreases the duration of the transmit periods based on an increase to the SNR and increases the duration of the transmit periods based on a decrease to the SNR.

In some implementations, the ultrasound transducer is further configured to operate in a sleep mode that comprises deactivation of transmission of at least some of the ultrasound signals, and wherein the control component controls switching operation of the ultrasound transducer between the sleep mode and the active mode based on a usage status of the FSD. In this regard, the usage status of the FSD can comprise an active usage status in which the FSD is positioned on the external body of the mother and an inactive usage status in which the FSD is not positioned on the external body of the mother, and wherein the computer executable components further comprise a usage status detection component that determines whether the usage status comprises the active usage status or the inactive usage status, and wherein the control component activates the active mode and deactivates the sleep mode based on the usage status being the active usage status and activates the sleep mode and deactivates the active mode based on the usage status being the inactive usage status.

In some embodiments, elements described in connection with the disclosed FSD can be embodied in different forms such as a computer-implemented method, a computer program product, or another form.

DESCRIPTION OF THE DRAWINGS

FIG. 3 presents a flow diagram of an example transmission power optimization process, in accordance with one or more embodiments of the disclosed subject matter.

FIG. 8 illustrates a block diagram of an example, non-limiting computer implemented method that facilitates reducing power consumption by a FSD, in accordance with one or more embodiments of the disclosed subject matter.

FIG. 9 illustrates a block diagram of another example, non-limiting computer implemented method that facilitates reducing power consumption by a FSD, in accordance with one or more embodiments of the disclosed subject matter.

FIG. 10 illustrates a block diagram of an example, non-limiting computer implemented method that facilitates estimating the depth of the fetal heart and reducing power consumption by a FSD, in accordance with one or more embodiments of the disclosed subject matter.

FIG. 11 illustrates a block diagram of another example, non-limiting computer implemented method that facilitates reducing power consumption by a FSD, in accordance with one or more embodiments of the disclosed subject matter.

DETAILED DESCRIPTION

Figure 1:
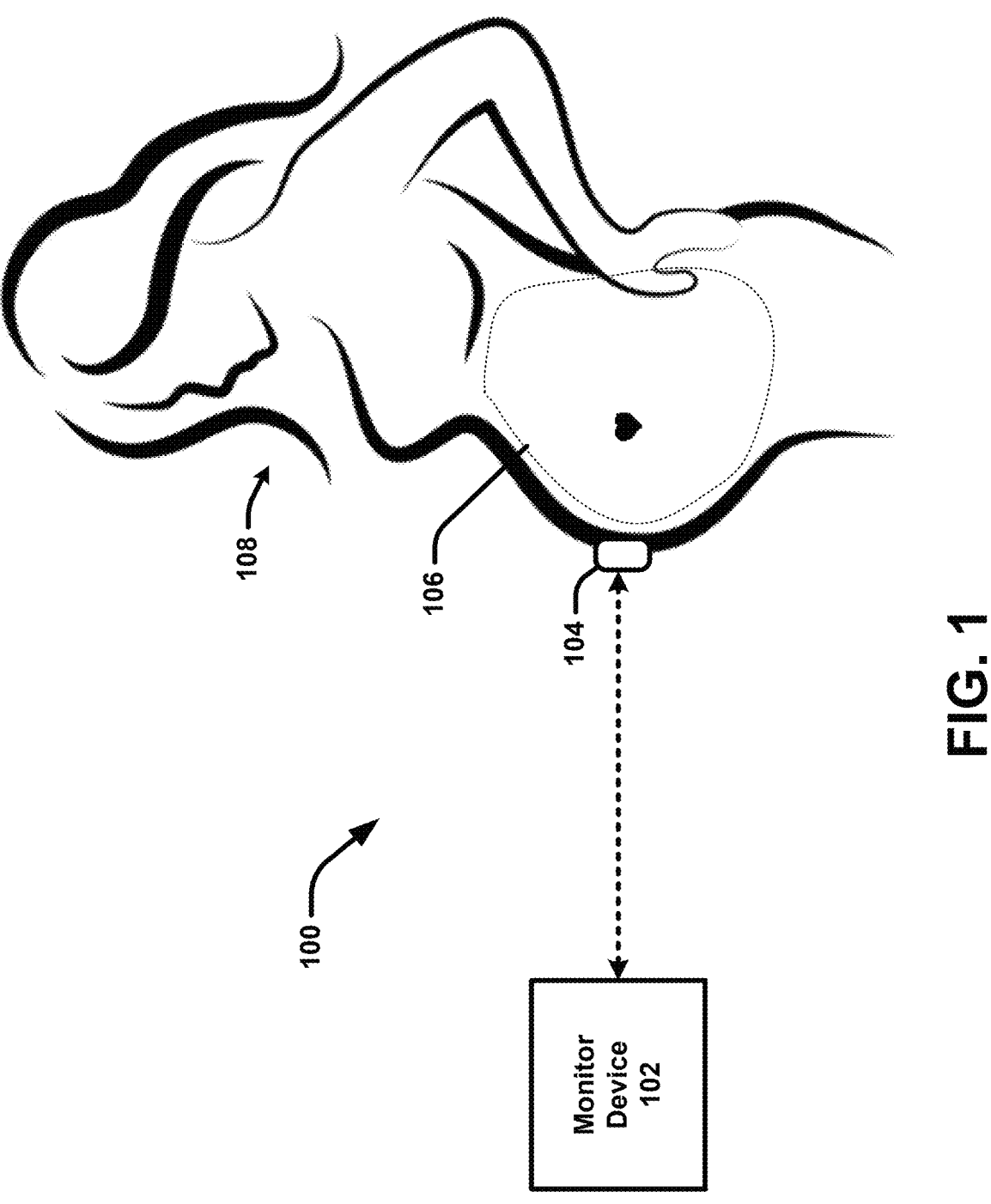
FIG. 1 presents an example fetal monitoring system (FMS) in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The subject disclosure provides systems, computer-implemented methods, apparatus and/or computer program products that facilitate reducing power consumption by fetal ultrasound transducers for extended battery life. A fetal sensor device (FSD) employed for fetal heart monitoring uses an ultrasound transducer that operates based on the doppler effect for the detection of fetal heart rate and other fetal parameters (e.g., fetal movement, fetal depth and other potential parameters). Typically, the transducer transmits an ultrasound carrier signal of a given amplitude in a pulsed manner for a fixed period of transmission time, referred to herein as the transmit (Tx) period. The same transducer is then used to receive reflected signals that are doppler shifted due to the movement of the heart tissues of the fetus in a receive window or receive (Rx) period. Using a demodulation technique, the carrier signal is stripped out of the reflected signals received during the receive period and the doppler shift due to the movement of the heart tissues identified. Correlation or peak detect algorithms are then utilized to extract the fetal heart rate from this extracted signal. Usually, the transmit pulse repetition rate (PRR) is in the range of about 2.0 kilohertz (hKz) to about 4.0 kilohertz (kHz) in such doppler ultrasound systems. Over the course of operation, the ultrasound transducer operates by continuously alternating between Tx and Rx periods to track the FHR over the duration of a monitoring session.

The transmit signal is one of the major contributors to the high-power draw of the transducers. For battery driven wireless FSDs with limited energy storage capacity, it is important to cut down on power consumption for extending battery operation without compromising performance of the FSD. Reducing the power consumed by the FSD is also of interest in a FMS wherein the FSD is wired to and receives power from an external power source (e.g., the monitor device or another power source) with limited energy supply, such as in the case of a battery operated monitor device for portable FMS applications.

The disclosed subject matter provides mechanisms for reducing the power consumption of the ultrasound transducer of an FSD without compromising on the pickup sensitivity, and thus extending the duration of monitoring between battery changes or charges. For example, as applied to battery driven wireless FSDs, the caregiver will thus have to replace or recharge the battery or battery pack less frequently, allowing for longer periods of uninterrupted monitoring during labor. The disclosed mechanisms can also be employed by wired FSDs that received power from an external source via wired connections to minimize power consumption from the external source (e.g., an external source with restricted power supply, such as a battery-operated external source). The disclosed mechanisms also optimize the amount of ultrasonic energy delivered into the mother's abdomen, without compromising the signal fidelity, and thus can be applied to both wireless and wired FSDs to optimize the amount of ultrasonic energy delivered into the mother abdomen. Lower power consumption also helps the transducer run cooler, which facilities extending life of the FSD components and prevents overheating, as applied to both wireless and wired FSDs.

In various embodiments, the disclosed techniques control both the amplitude or transmission power of the Tx signals and the duration of the Tx period to optimize the power consumption. In some implementations, the disclosed techniques use the signal-to-noise ratio (SNR) values of the received signals as a process variable to provide a control process that slowly reduces the Tx power until a minimum SNR threshold is reached that still enables accurate detection of the FHR. This is achieved by reducing the amplitude of the Tx signal drive. The reduced Tx power translates to a reduction in power consumption. If the FHR is lost or intermittent, the transducer can be reset to higher power immediately.

The disclosed techniques can also estimate the depth of the fetal heart in focus by adapting the duration of the Tx periods and observing how changes to the duration influence the SNR of the received signals, a process referred to herein as dynamic Tx windowing. As described in greater detail below, the Tx periods can be defined by a fixed duration and the duration of the Tx periods that is adapted can correspond to the active duration of a window or portion (referred to herein as the active portion) of the fixed duration over which the ultrasound transducer actively transmits ultrasound pulses, wherein the remainder of fixed duration excluding the active portion the ultrasound transducer is configured to not transmit ultrasound pulses. To this end, in some implementations, the depth of the fetal heart in focus can be estimated by sequentially adjusting (e.g., decreasing) the duration and/or position of the active portion relative to the fixed start and end times of the fixed duration while observing how the adjustments influence the SNR of the received signals until an optimal active portion duration/position is found that results in an optimal SNR value or value range of the received signals (e.g., wherein the optimal SNR value or value range satisfies defined SNR optimization criteria). The FSD can further set the ultrasound transducer to operate using the optimal active portion duration/position once determined. The depth of the fetal heart can further be estimated based on previously defined information correlating the optimal duration/position of the active portion to a corresponding fetal heart depth. The reduced Tx period, that is the active portion of the Tx period, translates to lower power consumption as the transducer is being excited for a shorter amount of time. The depth estimation and dynamic Tx windowing also minimizes the undesirable detection of artifacts by the transducer, such as the maternal heart rate (MHR) and other potential artifacts.

In some embodiments, the disclosed techniques also provide a sleep mode for the FSD in which transmission is deactivated when the FSD not in use, thus significantly minimizing power consumption, with automated switching between the sleep mode and the active sensing mode. For example, the FSD can be configured with a smart turn on feature that detects the instance of the FSD being placed on the mother's belly or the FSD being touched/repositioned by the clinician and activates the active sensing mode. Likewise, based on detection of the FSD being no longer used for an active monitoring session, such as being removed from a mother's belly for longer than a defined idle period (e.g., 1.0 minute, 3.0 minutes, or another defined time period), the FSD can be configured to automatically enter the sleep mode.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 presents an example FMS 100 in accordance with one or more embodiments of the disclosed subject matter. The FSM 100 includes a monitor device 102 and a fetal sensor device (FSD) 104. The FSD 104 corresponds to a small, non-invasive medical device comprising an ultrasound transducer configured to measure signals representative of one or more fetal parameters of a fetus using doppler-based ultrasound technology in association with placement of the FSD 104 on the external body of the mother 108. The one or more fetal parameters measured by the FSD 104 can include, but are not limited to, FHR, fetal movement, and fetal depth. For example, the FSD 104 is typically placed on the external surface of the abdomen to allow the mother 108 to comfortably lay on her back during the monitoring session. However, in some implementations, the FSD 104 may be positioned on the side body and/or the mother's back. The FSD 104 may be held in place using straps or another suitable mechanism once the FSD has been placed in an optimal position on the mother's body in which it is accurately picking up the heart rate of the fetus in focus.

Over the course of a fetal monitoring session, the FSD 104 can be configured to send raw and/or processed signal data representative of the one or more fetal parameters to the monitor device 102 for additional processing and/or rendering via one or more suitable output devices of the monitor device 102 (e.g., a display, a speaker, etc.). Additionally, or alternatively, some or all of the signal processing can be performed by the monitor device 102. For example, the FSD 104 can be configured to send raw doppler shifted signals to the monitor device 102 for signal processing and/or send partially processed signals (e.g., demodulated signals, digitized signals, etc.) to the monitor device 102 which in turn can process the raw or partially processed signals to calculate the FHR, fetal movement, fetal position/depth, and so on. With these embodiments, any information determined by the monitor device 102 based on processing of the raw or partially processed signals (and/or other information, such as control commands, configuration commands, context information, etc.) may be communicated back to the FSD 104 for usage thereof in association with adapting the operating parameters thereof (e.g., the Tx power, the Tx period duration, the position of the active portion of the Tx period, and/or the operating mode, either active mode or sleep mode) in accordance with the disclosed power optimization protocol.

The monitor device 102 and the FSD 104 can be communicatively coupled via any suitable wired or wireless communication technology. For example, in some embodiments, the FSD 104 includes or corresponds to a wireless FSD powered via an onboard power source, such as one or more batteries. In some implementations of these embodiments, the monitor device 102 and the FSD 104 can respectively be configured to communicate information between one another using any suitable wireless communication technology, such as but not limited to: Bluetooth™, Wireless Fidelity (Wi-Fi), near field communication (NFC), Zigbee™, Z-Wave™, infrared (IR), ultra-wideband (UWB), body area network (BAN) communication technologies, medical body area network (MBAN) communication technologies, cellular, and various other existing and foreseen wireless communication technologies. In some embodiments, the wireless communication technology can include a wireless communication technology tailored for performance under water to enable usage of the FSD 104 for monitoring FHR data in water birth scenarios. Additionally, or alternatively, the FSD 104 and the monitor device 102 may be communicatively coupled to one another via one or more wired communication technologies. In some implementations of these embodiments, the FSD 104 can receive power from the monitor device 102 via one or wired power connections and/or another external power source via one or more wired power connections.

In the example embodiment illustrated in FIG. 1, a single FSD 104 is being used in the context of a single fetus (represented by the heart symbol depicted within the womb 106 of the mother 108). However, the FMS 100 can be tailored to different usage scenarios involving simultaneously monitoring different numbers of fetuses and thus different numbers of FSDs 104, one or for each fetus. For example, the FMS 100 can be tailored in association with using a single FSD 104 to monitor a single fetus, two FSD 104 to respectively monitor two fetuses (i.e., twins), three FSD 104 to respectively monitor three fetuses (i.e., triplets), four FSDs 104 to respectively monitor four fetuses (i.e., quadruplets), and so on.

The FSD 104 can include suitable hardware and/or software that enables the operations described with respect to the FSD 104 as disclosed herein. For example, in some embodiments, FSD 104 can include an onboard power source (e.g., one or more batteries or another suitable power source), a memory and processor that enable onboard signal processing functionality and other computer-executable functions described herein, wireless or wired communication hardware and software that enable wired and/or wired communication between the FSD 104 and the monitor device 102, one or sensors that provide for sensing various parameters associated with the FSD, the mother 108 and/or the fetus (e.g., proximity sensors, contact sensors, temperature sensors, motion sensors, etc.), and other suitable hardware and/or software described with reference to FIG. 2.

Figure 2:
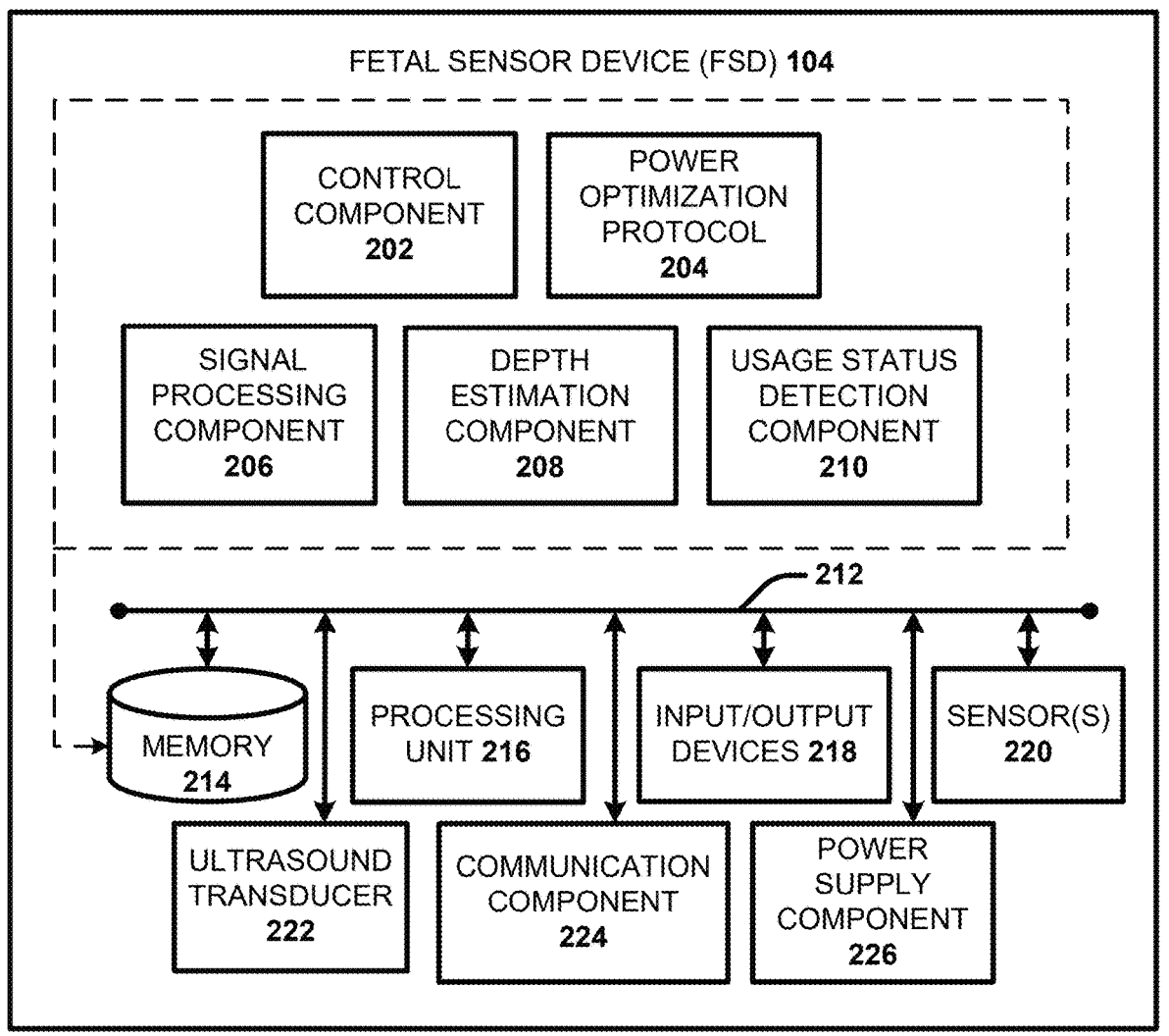
FIG. 2 illustrates a block diagram of an example, non-limiting fetal sensor device (FSD) of a FMS in accordance with one or more embodiments of the disclosed subject matter.

FIG. 2 illustrates a block diagram of an example, non-limiting FSD 104 in accordance with one or more embodiments of the disclosed subject matter. With reference to FIGS. 1 and 2, as mentioned with reference to FIG. 1, the FSD 104 can include an ultrasound transducer 222 configured to measure signals representative of one or more fetal parameters (e.g., FHR, fetal movement, fetal depth, and other potential parameters) of a fetus using doppler based ultrasound technology in association with positioning of the FSD 104 on an external body of the mother 108. The FSD 104 can further include memory 214 that stores machine-executable or computer-executable components or instructions embodied within one or more machines (e.g., embodied in one or more computer-readable storage media associated with one or more machines), and a processing unit 216 that executes the computer-executable components stored in the at least one memory 214. These computer-executable components can include (but are not limited to) control component 202, power optimization protocol 204, signal processing component 206, depth estimation component 208 and usage status detection component 210. Examples of said memory and processor as well as other suitable computer or computing-based elements, can be found with reference to FIG. 12 (e.g., processing unit 1204 and system memory 1206 respectively), and can be used in connection with implementing one or more of the systems or components shown and described in connection with FIGS. 1 and 2, or other figures disclosed herein.

In some implementations, the FSD 104 can include one or more input/output devices 218 to facilitate manually configuring the device and displaying data (e.g., operating settings, fetal parameters, battery level, etc.) to users in association with usage of the FMS 100. Suitable examples of the input/output devices 218 are described with reference to FIG. 12 (e.g., input devices 1228 and output device 1236). The FSD 104 can also include a communication component 224 that includes or corresponds to hardware and/or software that enables wired and/or wireless communication between the FSD 104 and the monitor device 102, and optionally enables wired and/or wireless communication between the FSD 104 and other FSDs activated for the monitoring session in a peer-to-peer fashion (e.g., as applied to monitoring two or more fetuses simultaneously). In some embodiments (e.g., in which the FSD 104 corresponds to a wireless device), the FSD 104 can also include a power supply component 226 that corresponds to any suitable onboard power source (e.g., one or more batteries, one or more rechargeable batteries, or another suitable power source).

The FSD 104 can also include one or more sensors 220. In various embodiments, the one or more sensors can include or correspond to various sensors configured to measure information indicative of the usage status of the FSD 104. For example, in various embodiments, the usage status can include an active usage status in which the FSD 104 is placed on the external body of the mother 108 and/or being repositioned relative thereto in association with usage of the FSD in an active mode wherein the FSD actively measures and monitors one or more fetal parameters (e.g., using the ultrasound transducer 222) in association with usage thereof for an active fetal monitoring session. The usage status can also include an inactive usage status in which the FSD 104 is not being used for an active fetal monitoring session (e.g., wherein the FSD 104 is not placed on the external body of the mother 108 and/or being repositioned relative thereto in association with actively measuring and monitoring one or more fetal parameters). As described in greater detail below, in some embodiments, the FSD can be configured to operate in a sleep mode during the inactive usage status, wherein the sleep mode comprises deactivation of transmission of at least some ultrasound signals by the ultrasound transducer 222 for conserving power during the inactive usage status.

In this regard, the one or more sensors 220 can include one or more contact sensors, one or more capacitive sensors, one or more proximity sensors, one or more motion sensors, one or more temperature sensors, or the like, that facilitate detecting (e.g., via the usage status detection component 210) when the FSD 104 is placed or not placed on the external body of the mother 108 and/or being touched/repositioned by the clinician (or another person). For example, in some implementations, based on changes to impedance levels associated with ultrasound signals transmitted by the ultrasound transducer 222 (e.g., as described in greater detail below with respect to the usage status detection component 210), one can detect whether the FSD is contacting the skin of the mother (or not). In another example, the one or more sensors 220 can include a proximity sensor and/or a capacitive sensor that facilitates detecting touching the FSD by a clinician (e.g., in association with placing and/or repositioning the FSD on the external body of the mother). Additionally, or alternatively, the one or more sensors 220 can include one or more motion sensors (e.g., an accelerometer, a gyroscope, an infrared sensor, and/or other types of motion sensors) that can facilitate detecting when 104 is placed or not placed on the external body of the mother (e.g., by the usage status detection component 208 based on monitored movement and/or motion patterns of the FSD 104.

The FSD 104 can further include a system bus 212 that couples the memory 214, the processing unit 216, the input/output devices 218, the one or more sensors 220, the ultrasound transducer 222, the communication component 224 and the power supply component 226 to one another.

With reference to the ultrasound transducer 222, in association with operating in an active mode of the FSD 104 in which the FSD 104 is being used actively for a fetal monitoring session, the ultrasound transducer 222 emits ultrasound waves and receives reflected and ultrasound waves that are reflected from one or more targeted tissues within the womb 106, which in this context includes the fetal heart, represented in FIG. 1 (and other figures) via the heart symbol. More particularly, the ultrasound transducer 222 comprises a transmitter/receiver element, typically comprising one or more crystals and/or a piezoelectric element, that generates ultrasound waves when an electric current is applied to it (e.g., via the power supply component 226 or another power source such as an external, wired power source in some embodiments). The transmitter/receiver element is integrated within a head portion of the FSD housing that is placed in direct contact with the mother's skin. The transmitter/receiver element of the transducer 222 transmits an ultrasound carrier signal of given carrier frequency and amplitude in a pulsed manner over a Tx period. The transmit pulse repetition rate (PRR), a configurable operating parameter of the ultrasound transducer 222, controls the repetition frequency of the ultrasound pulses transmitted over the Tx period. In various embodiments, the PRR can vary and is typically in the range of about 2.0 kHz to about 4.0 kHz.

The carrier frequency, also a configurable parameter of the ultrasound transducer 222, refers to the frequency band of the emitted ultrasound signals. In preferred embodiments, the carrier frequency of the ultrasound transducer 104 is restricted to one or more low or narrowband frequencies, preferably less than 5.0 megahertz (MHz), more preferably less than 4.0 MHz, more preferably less than 3.0 MHz and even more preferably less than 2.0 MHz. For example, in some implementations, the ultrasound transducer 222 can be configured to employ one or more narrowband carrier frequencies within a frequency range between about 1.0 MHz and about 2.0 MHz. Narrowband transducers are often used in doppler ultrasound for FHR monitoring due to their specific advantages in capturing and analyzing the doppler signals associated with blood flow and tissue movement. For example, narrowband transducers within a specific frequency range (e.g., about 1.0 to about 5.0 MHz), allow for a more focused detection of the doppler signals related to blood flow and tissue movement in the fetal heart. This can result in a higher signal-to-noise (SNR) ratio, enhancing the accuracy of FHR measurements.

The amplitude of the transmitted ultrasound waves, also a configurable parameter of the ultrasound transducer 222, refers to the strength or intensity of the ultrasound signal. The amplitude of the ultrasound signal influences the sensitivity of the ultrasound transducer 222, wherein the sensitivity refers to the ability of the ultrasound transducer 222 (or more particularly the signal processing component 206) to accurately detect and compute the FHR based on the received, doppler-shifted ultrasound signals. In this regard, stronger ultrasound signals (e.g., higher amplitude signals) are better at penetrating through tissues (e.g., abdominal tissues of the mother) and thus are associated with lower attenuation and stronger received doppler shifted signals by the ultrasound transducer 222 as compared to weaker ultrasound signals (e.g., lower amplitude signals). However, the stronger the amplitude of the transmitted ultrasound signals, the greater the amount of ultrasonic energy delivered into the mother's abdomen.

In accordance with one or more embodiments, the FSD 104 can control (e.g., via control component 202) the amplitude of the transmitted ultrasound waves as a function of controlling the amount of power (e.g., referred to herein as the transmission power) supplied to the ultrasound transducer 222 (e.g., via the power supply component 226 or another power source) in association with generating and transmitting the ultrasound waves by the ultrasound transducer 222. As described in greater detail below, in one or more embodiments, the control component 202 can dynamically adjust (e.g., decrease and increase) the transmission power (and thus the amplitude) of the ultrasound signals transmitted during the active mode of the FSD 104 as needed in accordance with a transmission power optimization process (e.g., defined via the power optimization protocol 204) that facilities minimizing power consumption by the ultrasound transducer 222 while also ensuring signal fidelity.

The transmitter/receiver element of the ultrasound transducer 222 also receives any reflected ultrasound waves that may be reflected by tissues of the body, including the targeted fetal heart, over an Rx period following the Tx period. Due to the motion of the fetal heart (which beats rhythmically), the frequency of the reflected ultrasound waves is slightly shifted (doppler shifted) compared to the emitted waves. This shift is proportional to the speed of membrane/tissue movement of the fetal heart. These shifts can be detected and used to calculate the fetal heart rate (FHR) and fetal movement (e.g., via signal processing component 206) based on the repetition rate of the frequency changes using one or more algorithms. For example, using a demodulation technique, the signal processing component 206 can remove the carrier signal from the reflected signals and extract the doppler shift due to the movement of the heart tissues. Correlation and/or peak detect algorithms are then utilized to extract the fetal heart rate from this extracted signal. Over the course of operation in the active mode, the ultrasound transducer 222 operates by continuously alternating between Tx and Rx periods to track the FHR over the duration of a monitoring session.

The transmit signal is one of the major contributors to the high-power draw of doppler-based fetal ultrasound transducers, such as ultrasound transducer 222. For battery driven wireless FSDs (e.g., FSD 104 in some embodiments) with limited energy storage capacity, it is important to cut down on power consumption for extending battery operation without compromising performance of the FSD.

In various embodiments, the control component 202 can control operations of the ultrasound transducer 222 in accordance with a power optimization protocol 204 that facilitates for reducing the power consumption of the ultrasound transducer 222 without compromising on the pickup sensitivity, and thus extending the duration of monitoring between battery changes or charges in embodiments in which the FSD corresponds to a wireless FSD. The power optimization protocol 204 also optimizes the amount of ultrasonic energy delivered into the mother's abdomen, without compromising the signal fidelity, and thus can be applied to wired FSDs that receive power from an external source to optimize the amount of ultrasonic energy delivered into the mother abdomen. Lower power consumption also helps the ultrasound transducer 222 to run cooler, which facilities extending life of the FSD components and prevents overheating, as applied to both wireless and wired FSDs.

In various embodiments, the power optimization protocol 204 defines one or more active mode optimization processes that facilitate optimizing (e.g., minimizing) power consumption by the FSD 104 during the active mode. The one or more active mode optimization processes can involve controlling and/or adjusting (e.g., via control component 202) the amplitude or transmission power of the Tx signals and/or the duration of the Tx periods. To this end, the control component 202 can be configured to control (e.g., adjust and set) the transmission power of the Tx signals and/or the duration of the Tx periods during the active mode in accordance with the one or more active mode optimization processes as defined via the power optimization protocol 204.

In some embodiments, the one or more active mode power optimization processes defined via the power optimization protocol 204 can include a transmission power optimization process that comprises adjusting (e.g., via control component 202) the transmission power (and thus the amplitude) of the ultrasound signals transmitted by the ultrasound transducer 222 during the Tx periods based on the SNR value or values of the reflected signals of the ultrasound signals received during the Rx periods, or more particularly the SNR values of the received signals over a period of time accounting for a plurality of sequential Rx periods. For example, the reflected signals are generally aggregated across a plurality of Rx periods within a defined period of time (e.g., every 1.0 minute or another defined and optionally adaptable time period), preprocessed (e.g., demodulated, filtered, transformed, etc.), and thereafter the signal processing component 206 calculates an SNR value of the aggregated signals for the corresponding defined period of time. To this end, the transmission power optimization process uses the SNR values of the received signals over time as a process variable and directs the control component 202 to slowly reduce (e.g., at a rate defined via the power optimization protocol 204) the Tx power of the transmitted ultrasound signals (e.g., and thus the amount of power consumed) until a minimum SNR threshold (e.g., defined in the power optimization protocol 204) is reached that still enables accurate and consistent detection of the FHR.

With these embodiments, the signal processing component 206 can calculate the SNR values of the received/reflected ultrasound signals over time in association with calculating the FHR values based on the received/reflected signals. For example, the signal processing component 206 can continuously and in real-time, aggregate reflected signals received across a plurality of Rx periods within a defined period of time (e.g., every n microseconds or n seconds, every m duty cycles accounting for every m Tx periods, or another defined and optionally adaptable time period), optionally preprocess the aggregated signals (e.g., demodulate them, filter them with respect to noise, artifacts, etc., and/or transform them, etc.), and calculate an SNR value of the aggregated signals for the corresponding defined period of time. This results in an updated SNR value calculation every defined time period that reflects the current SNR of the incoming signals. Thus, updated SNR values representing the amount of signals of interest (e.g., fetal heartbeat signals, fetal movement signals, etc.) relative to the amount of noise (e.g., attributed to various factors such as maternal movement, signal reflections from other tissues, interference and others) are calculated every defined time period over the course of the monitoring session. The signal processing component 206 can employ any known or future SNR calculation process or algorithm to calculate the SNR value of the aggregated (and optionally preprocessed) signals.

The control component 202 can further monitor the SNR values and dynamically adjust the transmission power based on changes to the SNR. For example, in some embodiments, the control component 202 can increase the transmission power based on a decrease to the SNR and decrease the transmission power based on an increase to SNR.

Additionally, or alternatively, the control component 202 can monitor the SNR values and the FHR values to ensure they correspond to acceptable values (e.g., as defined in the power optimization protocol 204) in association with slowly reducing the transmission power. With these embodiments, the acceptable SNR values can be defined based on a minimum SNR threshold, such that SNR values exceeding the threshold are considered acceptable. Acceptable FHR values can be defined as FHR values that meet defined acceptability criteria with respect to consistency, and/or range of interest (e.g., between about 120 beats per minute (BPM) and 180 BPM, or another defined range of interest), where the noise levels do not inhibit the signal processing algorithm or algorithms (e.g., autocorrelation algorithms, peak detection algorithms, and others) used by the signal processing component 206 to calculate the FHR from the received signals (e.g., typically the aggregated signals over the defined time period).

For example, if a fetal heart is present in close proximity of the FSD (e.g., located within a relative shallow depth relative to the abdominal surface) and there is limited attenuation of the doppler shifted signals received due to the tissues of the abdomen, the signals received by the ultra- sound transducer 222 will be very strong with high SNR. Under such a scenario, the control component 202 can dynamically reduce the Tx power drive circuitry voltage (and hence the power consumed) while using the SNR as the process variable. If subsequently the FHR is lost or becomes inconsistent (e.g., meaning one or more of the FHR values calculated based on the received signals corresponding to an unacceptable FHR value) and/or the SNR values fall below the minimum SNR threshold (e.g., due to movement of the fetus away from the FSD for instance), the transmission power optimization process direct the control component 202 to reset the ultrasound transducer 222 to a higher transmission power immediately (e.g., the higher power value being defined by the power optimization protocol 204). The transmission power optimization process can further direct the control component 202 to continue with slowly reducing the transmission power again so long as the FHR values correspond to valid values and the minimum SNR value is not reached.

FIG. 3 presents a flow diagram of the transmission power optimization process 300, in accordance with one or more embodiments of the disclosed subject matter. With reference to FIGS. 1-3, transmission power optimization process 300 begins at 302 under the context that the FSD 104 is currently operating in the active mode, that the current FHR values determined based on the signals received during the Rx periods are acceptable, and that the minimum SNR threshold has not been reached. For example, in various embodiments, in association with initiating the active mode, the control component 202 can be configured to set the transmission power to a default power value. In some implementations, the default power value can correspond to a maximum, high power value (e.g., as defined in the power optimization protocol).

With this context in mind, at 302, process 300 comprises reducing, by a FSD comprising a processor (e.g., FSD 104), a transmission power of ultrasound signals transmitted by an ultrasound transducer (e.g., ultrasound transducer 222) of the FSD during an active mode of the FSD. At 304, process 300 comprises determining, by the FSD (e.g., using signal processing component 206), one or more SNR values asso- ciated with reflected signals of the ultrasound signals received by the ultrasound transducer over time in associa- tion with the reducing, and determining, by the FSD (e.g., using signal processing component 206), FHR values based on the reflected signals of the ultrasound signals in associa- tion with the reducing. For example, the reducing at 302 can include or correspond to reducing the transmission power from the default power values by a defined amount or percentage (e.g., as defined via the power optimization protocol 204), and the determining the one or more SNR values at 304 can include or correspond to determining SNR values associated with the signals received following the transmission power reduction by the defined amount or percentage.

At 306, the FSD determines (e.g., via the control com- ponent 202) whether the FHR values are acceptable (e.g., with respect to consistency, range, and/or other defined criteria, as defined in the power optimization protocol 204), and at 310, the FSD determines (e.g., via the control component 202) whether the minimum SNR threshold has been reached (e.g., as defined via the power optimization protocol 204). To this end, the determination of the whether the FHR values are acceptable at 306 inherently accounts for the SNR values being acceptable (e.g., and not below the minimum SNR threshold), as unacceptable SNR values (i.e., SNR values below the minimum SNR threshold) would likely result in an inability to calculate/detect and/or accu- rately and consistently detect the FHR. In various embodi- ments, the determination of whether the FHR values are acceptable at 306 can be based on a single FHR value, a number of FHR values (e.g., consecutive and/or non-con- secutive), or none at all (e.g., when the FHR value is undetectable) as defined in the power optimization protocol 204). Likewise, the determination of whether the minimum SNR threshold is reached at 310 can be based on a single SNR value or a number of SNR values (e.g., consecutive and/or non-consecutive), as defined in the power optimiza- tion protocol 204).

If at 306 the FSD determines that the FHR values are acceptable, and at 310 the FSD determines that the minimum SNR threshold has not been reached, then process 300 continues back to 302. To this end, in association with continuing back to 302, the reducing operation of 302 corresponds to further reducing the transmission power of the ultrasound signals transmitted during the active mode by the defined amount or percentage (or another defined amount or percentage, as defined via the power optimization protocol). For example, as noted above, the transmission power optimization process can direct the control compo- nent 202 to slowly reduce the transmission power over the course of operation of the FSD. To this end, processes 300 corresponds to reducing the transmission power, checking the SNR and FHR values, and then continuing to incremen- tally reduce the transmission power so long as the FHR values are acceptable until the minimum SNR has been reached so long as the FHR values are acceptable. The rate at which the transmission power is reduced can be defined in the power optimization protocol 204 and account for the amount of reduction in transmission power as a function of time and/or duty cycles of the active mode (e.g., reduce the transmission power by a defined percentage every defined time frame).

However, if at 306 the FSD determines that the FHR are unacceptable (e.g., process 300 continues to 308, and the FSD resets (e.g., via control component 202) the transmis- sion power of the ultrasound signals to a maximum power level (e.g., or another defined higher power level, as defined via the power optimization protocol 204) and maintains operation of the FSD in active mode. In this regard, step 308 corresponds to increasing the power level of the transmitted ultrasound signals. At 314, the FSD continues to determine the SNR values of reflected signals of the ultrasound signals received by the ultrasound transducer and the corresponding FHR values in association with the maintaining (e.g., at the maximum or higher power level). Process 300 thereafter continues back to 306 and proceeds accordingly.

If at 310 the FSD determines that the minimum SNR threshold is reached, then process 300 continues to 312, wherein the FSD sets (e.g., via the control component 202) the transmission power of the ultrasound signals to the current transmission power level and maintains operation by the FSD in the active mode at the current transmission power level. Process 300 further continues to 314, wherein the FSD continues to determine the SNR values of reflected signals of the ultrasound signals received by the ultrasound trans- ducer and the corresponding FHR values in association with the maintaining (e.g., at the current transmission power value). Process 300 thereafter continues back to 306 and proceeds accordingly.

With reference back to FIGS. 1 and 2, the one or more active mode power optimization processes defined via the power optimization protocol 204 can additionally, or alternatively, include one or more dynamic Tx windowing processes that control the duration of the Tx periods (e.g., as controlled via control component 202) employed by the ultrasound transducer 222 in a manner that facilitates minimizing power consumption by the ultrasound transducer 222. The one or more dynamic Tx windowing processes can involve adjusting the duration of the Tx periods based on the depth of the fetal heart targeted by the FSD 104 and/or the SNR values of the received signals. To this end, the depth of the fetal heart refers to the distance between the FSD 104, as positioned on the external body of the mother, and the fetal heart, as positioned within the womb 106. As the FSD is typically placed on the external surface of the abdomen, the depth of the fetal heart typically corresponds to the depth of the fetal heart from the surface of the abdomen (e.g., typically measured in centimeters). The duration of the Tx periods influences the sensing depth or depth coverage of the ultrasound transducer 222, as illustrated in FIGS. 4-6E.

Figure 4:
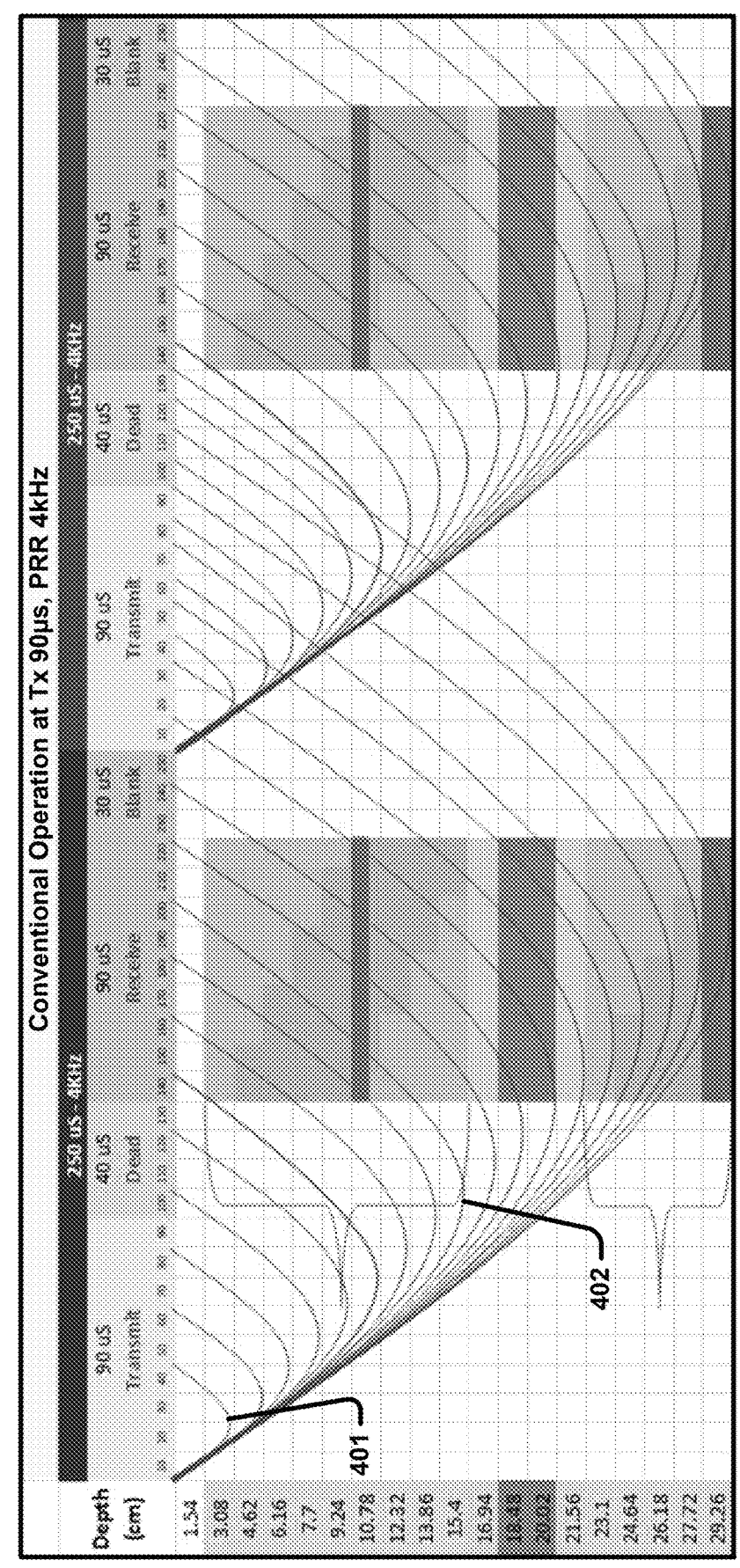
FIG. 4 presents a chart illustrating performance of an example ultrasound transducer in accordance with a conventional operating protocol, in accordance with one or more embodiments of the disclosed subject matter.

In this regard, FIG. 4 presents a chart 400 illustrating performance of an example ultrasound transducer corresponding to ultrasound transducer 222 in accordance with a conventional operating protocol, in accordance with one or more embodiments of the disclosed subject matter.

With reference to FIGS. 1-4, as illustrated in chart 400, a doppler-based fetal ultrasound transducer (e.g., corresponding to ultrasound transducer 222) typically operates in a cyclical manner with repeating duty cycles every defined time period (e.g., every 250 μs at the PRR of 4.0 kHz in accordance with this conventional example). Each duty cycle involves a transmit (Tx) period, followed by a dead period, followed by a receive (Rx) period and a blank period, wherein the dead period and the blank period respectively correspond to wait period in which the ultrasound transducer device does not transmit or receive. In accordance with this example timing schema, the duration of the Tx period is 90 μs, the duration of the dead period is 40 μs, the duration of the Rx period is 90 μs, and the duration of the blank period is 30 μs (e.g., making the total duration of each duty cycle 250 μs). During the Tx period, the ultrasound transducer emits ultrasound waves in a pulsed manner in accordance with a defined Tx pulse duty cycle (e.g., one pulse every n microseconds, such as every 1.0 μs, every 2.0 μs, every 3.0 μs or another defined Tx pulse duty cycle). As the emitted ultrasound waves encounter tissues in the abdomen, they are reflected back toward the transducer. Each pulse takes x amount of time to reach the targeted fetal heart and be reflected back to the transducer. If there is fetal heart at a given depth, the wave would reflect back towards the transducer and reach the transducer after the x amount of time.

As illustrated in chart 400, each parabola represents the travel of the first pulsed ultrasound wave over time (e.g., in microseconds, represented via the x-axis of chart 400) emitted at the start point of the Tx period (e.g., at about the 1.0 μs time point) into the abdomen. The base of each parabola indicates the point or depth (e.g., in centimeters (cm), represented via the y-axis or the vertical axis of chart 400) at which the emitted ultrasound wave is reflected back toward the ultrasound transducer as reflected by one or more tissues within the abdomen at the corresponding depth. The end point of each parabola represents the end time (e.g., along the x-axis of chart 400) at which the reflected wave is returned back to the transducer. To this end, the distance between the left and right endpoints of each parabola corresponds to the x amount of time over which the signal travels into the body following emission and returns back to the ultrasound transducer following reflection by fetal heart tissue at the corresponding depth. Naturally, this amount of time increases as the depth increases. For instance, as illustrated in chart 400, parabola 401 represents the emitted ultrasound wave as reflected by tissue at about 3.0 cm, which in this example takes about 40 us to travel to the 3.0 cm depth and be reflected back to the ultrasound transducer. In another example, parabola 402 represents the emitted ultrasound wave as reflected by tissue at about 15.0 cm, which in this example takes about 200 μs to travel to the 14.0 cm depth and be reflected back to the ultrasound transducer.

The ultrasound transducer 222 can only measure the FHR (and other fetal parameters, such as fetal movement) based on those signals which are bounced back from the targeted fetal heart and received during the Rx period. As indicated in chart 400, many of the pulsed waves are not received during the immediate receive period following the Tx period, as some are reflected back by other tissues in the body besides a targeted fetal heart and reflected back during the dead period. In addition, some of the ultrasound waves that travel deeper into the body are reflected back toward the transducer and reach the transducer after the immediate Rx period has passed (e.g., during the blank period during the next Tx period). To this end, the rest of the transmitted ultrasound waves are a waste of power. This phenomenon is more accurately illustrated in FIGS. 5A and 5B.

Figure 5A:
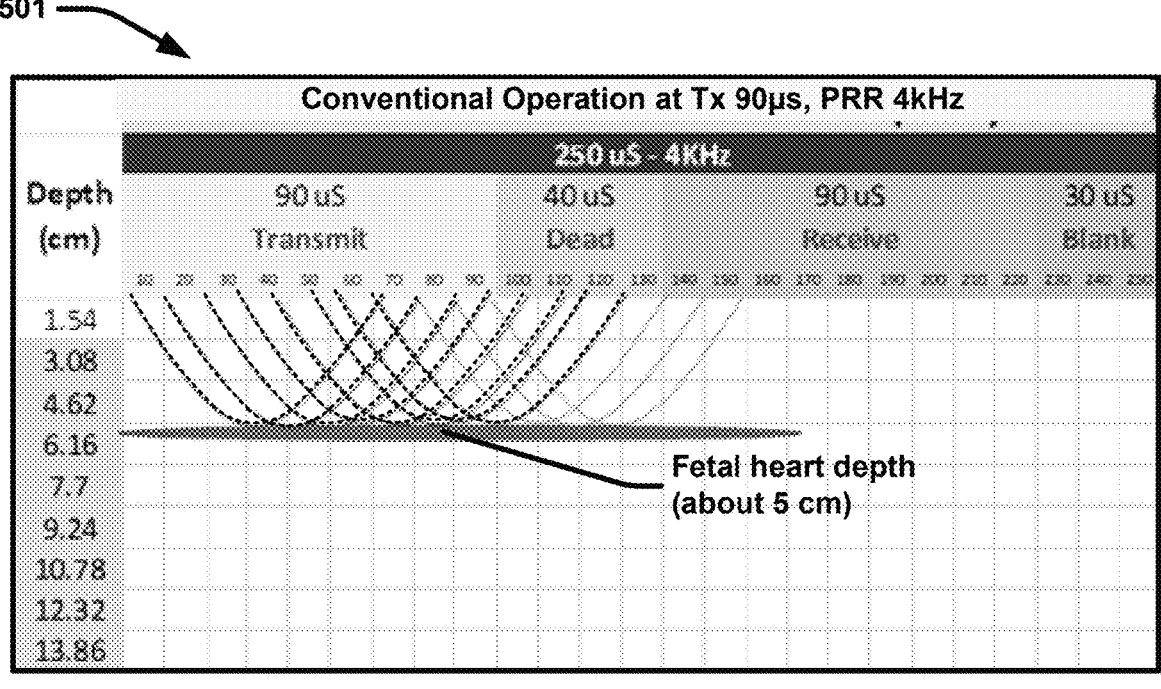
FIGS. 5A and 5B presents additional charts illustrating performance of an example ultrasound transducer in accordance with a conventional operating protocol, in accordance with one or more embodiments of the disclosed subject matter.
Figure 5B:
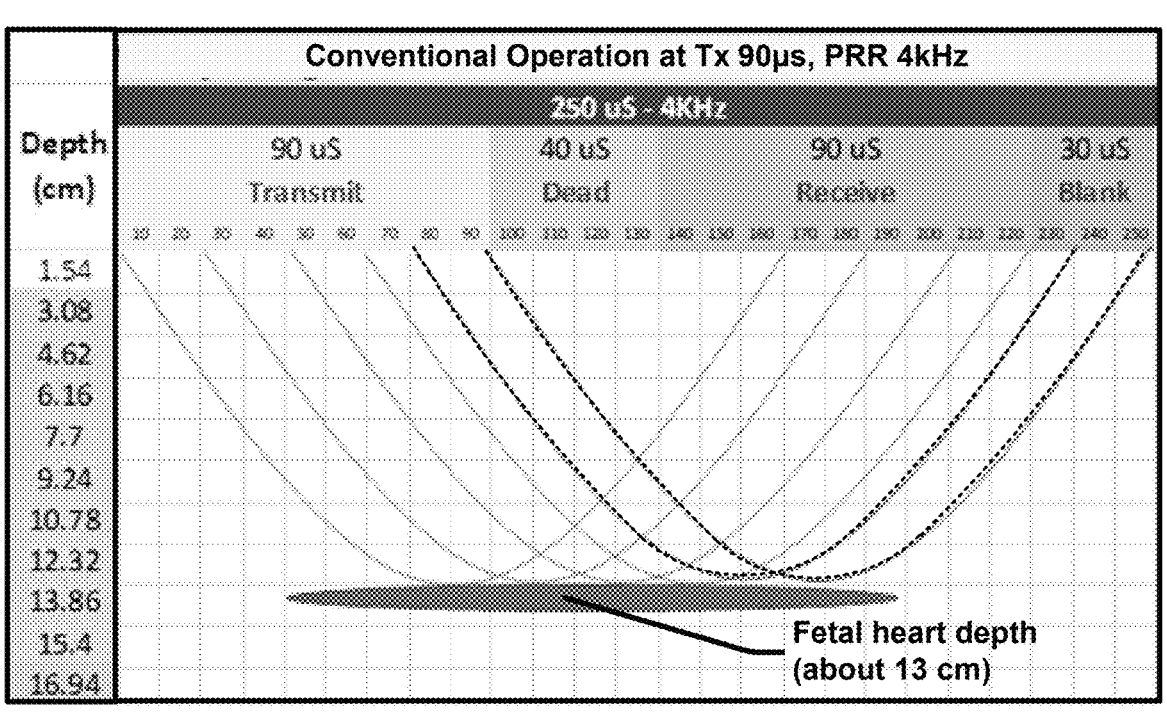

In this regard, FIGS. 5A and 5B present charts (e.g., chart 501 and chart 502, respectively) illustrating performance of an example ultrasound transducer corresponding to ultrasound transducer 222 in accordance with a conventional operating protocol, in accordance with one or more embodiments of the disclosed subject matter. As with chart 400, in these examples, the ultrasound transducer 222 is configured to operate in the same cyclical manner with repeating duty cycles in accordance with the same duty cycle (e.g., every 250 μs at the PRR of 4.0 kHz) and in accordance with the same time schema for the Tx periods, dead periods, receive periods and blank periods. With reference to FIGS. 5A and 5B, chart 501 demonstrates the how the ultrasound waves emitted over the duration of the Tx period (e.g., over the entirety of the 90 μs Tx period duration) travel into the body and are reflected back to the ultrasound transducer by a targeted fetal heart at a depth of about 5.0 cm. Chart 502 demonstrates the how the ultrasound waves emitted over the duration of the Tx period (e.g., over the 90 μs Tx period duration) travel into the body and are reflected back to the ultrasound transducer by a targeted fetal heart at a depth of about 13.0 cm. As illustrated in charts 501 and 502, each parabola represents an emitted ultrasound wave in accordance with a defined Tx pulse duty cycle, which in this example is about one wave every 10 μs for ease of illustration, however it should be appreciated that the Tx duty cycle can vary under different operating configurations (e.g., typically every 1.0 μs, or another suitable Tx pulse duty cycle) The left endpoint of each parabola represents the time of emission, the base of each parabola curve represents the fetal heart at the corresponding depth from which the emitted wave is reflected, and the right endpoint of each parabola represents the time at which the reflected wave is received back at the ultrasound transducer. In these examples, the ultrasound waves represented with the dashed lines correspond to those waves which are not received by the ultrasound transducer during the Rx period. In this regard, for the smaller depth corresponding to chart 501, only those few ultrasound waves emitted at the end of the Tx period (e.g., from about the 70th us time point to the 90th us time point) are actually received during the Rx period, while the rest are a waste of power. Likewise, for the larger depth corresponding to chart 502, only those ultrasound waves emitted at the beginning of the Tx period (e.g., from about the 1.0 μs time point to the $60^{th}$ μs time point) are actually received during the Rx period, while the rest are a waste of power.

To this end, in accordance with the conventional operating process, the duration of the Tx period is fixed, and depending on the depth of the heart only some of the transmitted waves are actually reflected back by the heart to the transducer during the Rx period. In accordance with one or more dynamic Tx windowing processes (e.g., defined via the power optimization protocol 204), the control component 202 can adapt the duration of the Tx periods depending on the depth of the fetal heart and/or the SNR values of the received signals. In accordance with some embodiments of the dynamic Tx windowing process, the concept of adapting the duration of the Tx periods corresponds to configuring the ultrasound transducer 222 (e.g., by the control component 202) to transmit ultrasound pulses for only portion of the available duration of the Tx period in which the transmitted pulses are reflected by the targeted fetal heart and received during the Rx period. This can involve configuring the ultrasound transducer 222 to only emit ultrasound waves over a portion of the Tx period and adapting the duration and position of the portion relative to the fixed start time and end time of the Tx period as previously defined and controlled in accordance with the conventional operating time schema employed. More particularly, in various embodiments, the Tx periods employed by the ultrasound transducer can be constrained by a first duration (e.g., 90 μs as with example charts 400, 501, and 502, or another defined duration), and wherein the duration of the Tx periods controlled by the control component 202 in accordance with the dynamic Tx windowing process correspond to a second duration within the first duration.

For example, as applied to the 5.0 cm depth scenario illustrated in chart 501, based on the depth of the fetal heart being around 5.0 cm, the control component 202 can configure the ultrasound transducer 222 to only emit ultrasound waves over the portion of the Tx period occurring between about the $70^{th}$ μs time point and the $90^{th}$ μs time point of the Tx period such that the ultrasound transducer does not emit the ultrasound waves corresponding to the dashed parabolas. Likewise, as applied to scenario illustrated in chart 502, based on the depth of the fetal heart being around 13.0 cm, the control component 202 can configure the ultrasound transducer 222 to only emit ultrasound waves over the portion of the Tx period occurring between about the 1.0 μs time point and the $70^{th}$ μs time point of the Tx period such that the ultrasound transducer does not emit the ultrasound waves corresponding to the dashed parabolas. By emitting ultrasound waves only over the portion of the Tx period as tailored based on the depth of the fetal heart, this results in decreasing power consumption by the ultrasound transducer 222 owing to the decreased amount of time over which the ultrasound transducer 222 actively generates and transmits ultrasound pulses, as illustrated in FIGS. 5A and 5B.

To this end, the second portion of the Tx period over which the ultrasound transducer actively transmits ultrasound waves is referred to herein as the active portion of the Tx period. Reference to tailoring or controlling the duration of the Tx period in accordance with one or more embodiments of the dynamic Tx windowing processes described herein corresponds to tailoring or controlling the duration of the active portion and/or the position of the active portion within the constrained first duration defined for the Tx period relative to the start point and end point of the first duration. In this regard, the dynamic Tx windowing process can involve decreasing or increasing the duration of the active portion within the constrained first duration, wherein as the duration of the active portion is decreased, so is the power consumption. The dynamic Tx windowing process can also involve moving the position of the active portion away from and/or towards the start time of the first duration, wherein the first duration is defined by a start time and end time, which in the example illustrated in FIGS. 5A and 5B correspond to 0 (or 0.1) μs and 90 μs, respectively. As noted above, the duration and position of the active portion can be tailored based on the depth of the fetal heart.

FIGS. 6A-6E present charts (e.g., charts 601-605 respectively) illustrating different example configurations for the active portion of the Tx period as tailored to different fetal heart depths, in accordance with one or more embodiments of the dynamic windowing process. In accordance with charts 601-605, the ultrasound transducer is configured to operate in accordance with the same time schema for the Tx, dead, blank and receive periods described above with reference to charts 400 and chart 500. Repetitive description is omitted for sake of brevity. However, it should be appreciated that the disclosed techniques can be tailored to other time schemas for the corresponding periods and other operating configurations of the ultrasound transducer 222 (e.g., with respect to PRR, and other parameters).

With reference to FIGS. 6A-6E in view of FIGS. 1-5B, FIG. 6A presents an example chart 601 corresponding to chart 501 with the ultrasound signals corresponding to the dashed lines removed. In this example, based on the fetal heart being at about 5.0 cm, in accordance with the dynamic Tx windowing process (as defined via the power optimization protocol 204) the control component 202 can tailor the active portion of the Tx period to include only the portion of the Tx period occurring between about the $70^{th}$ μs time point and the $90^{th}$ μs time point. For example, in some embodiments, the dynamic Tx windowing process defined in the power optimization protocol can define predetermined, optimal active portions (e.g., with respect to duration and position relative to the fixed start and end times of the fixed Tx active period) correlated to different defined depths under one or more different operating configurations for the ultrasound traducer 222 (e.g., with respect to time schema for the respective Tx, dead, receive and blank periods, PRR, operating transmission power, and other operating parameters). In some implementations of these embodiments, based on learned or known information identifying or indicating the current depth of the fetal heart (e.g., as determined via the depth estimation component 208 and/or determined using another mechanism), the control component 202 can be configured to apply the corresponding optimal active portion in association with configuring the transmission of the ultrasound transducer 222. In other embodiments, the control component 202 can dynamically determine the optimal active portion for a targeted fetal heart in association with estimating the depth and adapting the active portion using the SNR of the signals as a process variable, as described in greater detail below.

Figure 6A:
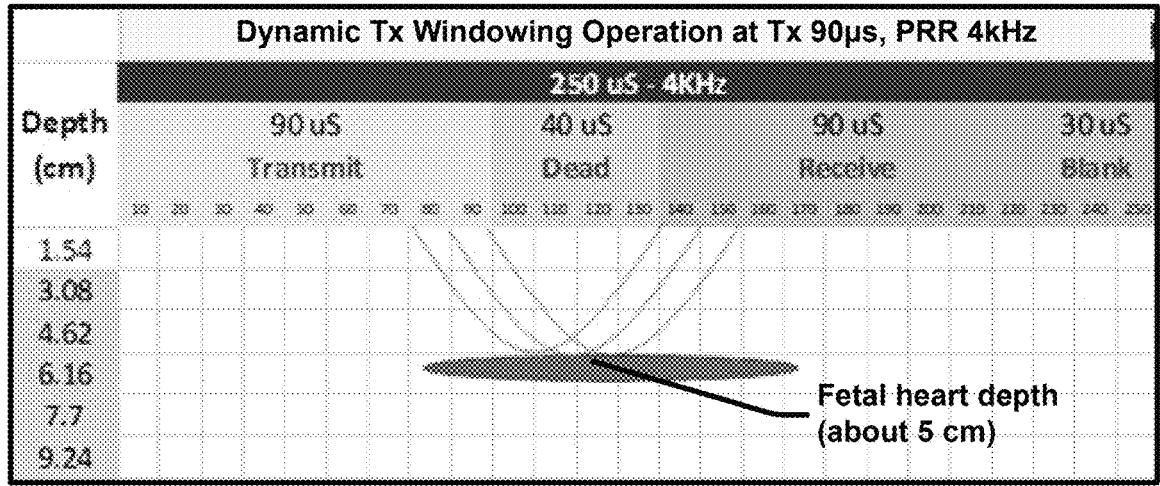
FIGS. 6A-6E present charts illustrating different example configurations for the active portion of the Tx period as tailored to different fetal heart depths, in accordance with one or more embodiments of a dynamic windowing process.
Figure 6B:
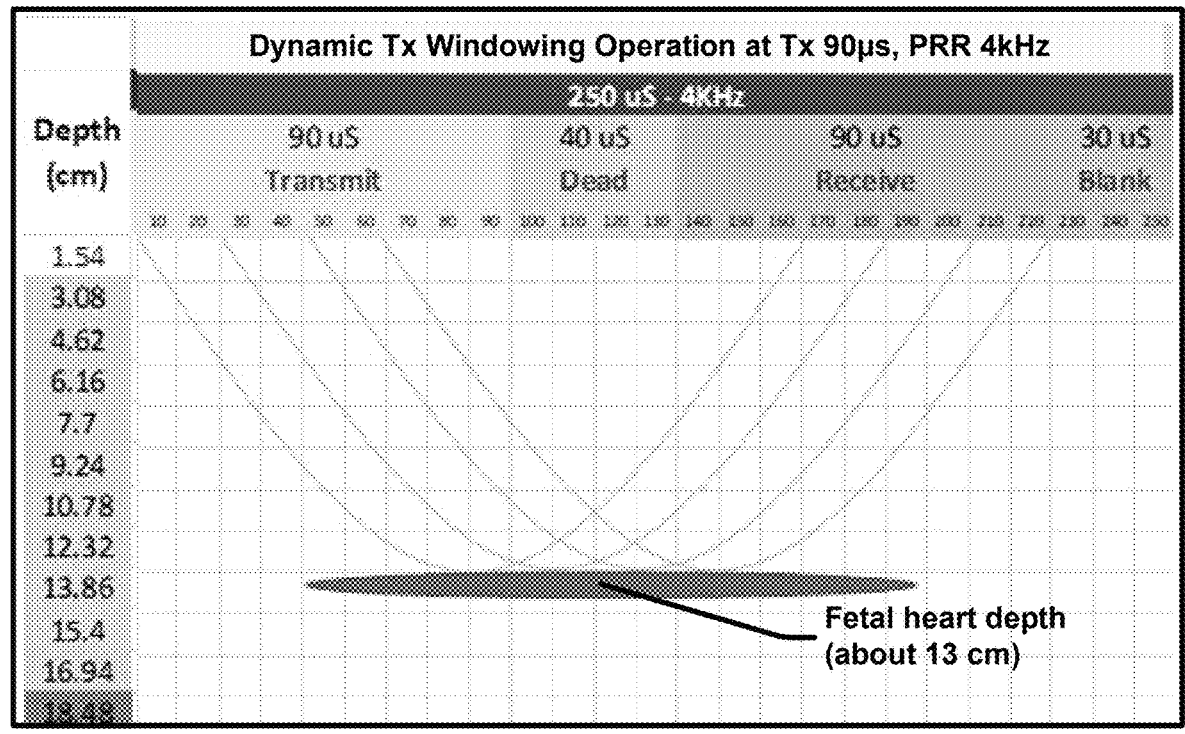

FIG. 6B presents an example chart 602 corresponding to chart 502 with the ultrasound signals corresponding to the dashed lines removed. In this example, based on the fetal heart being at about 13.0 cm, in accordance with the dynamic windowing process (as defined via the power optimization protocol 204) the control component 202 can tailor the active portion of the Tx period to include only the portion of the Tx period occurring between about the 1.0 μs time point and the 70$^{th}$ μs time point (e.g., in accordance with predefined optimal active portion criteria correlated to corresponding depths and/or in accordance with a dynamically adapting the active Tx period, as described below).

Figure 6C:
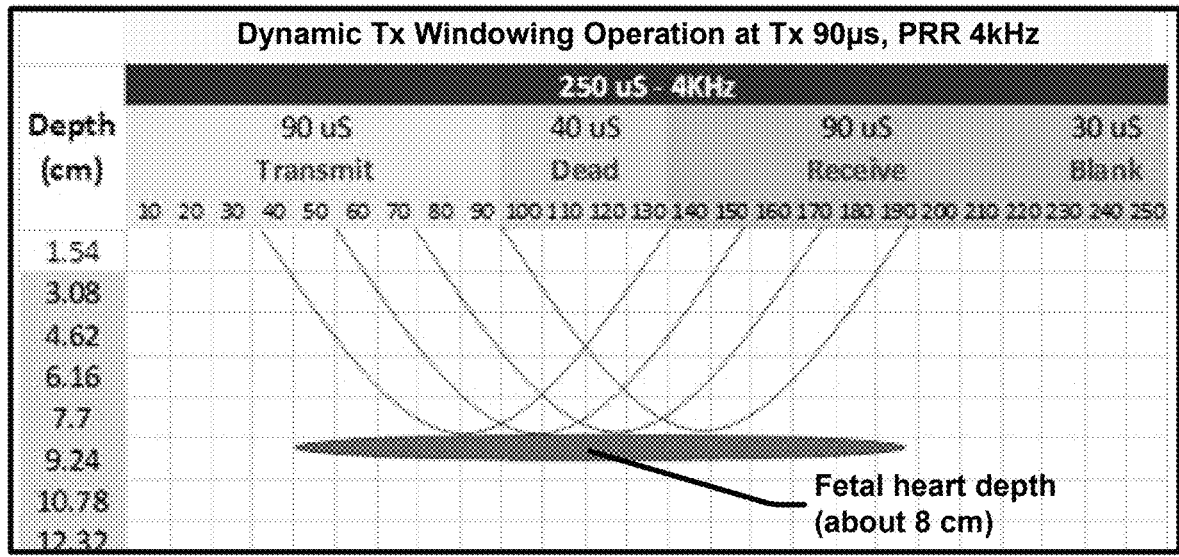

FIG. 6C presents another example chart 603 corresponding to a scenario in which the fetal heart is positioned at about 8.0 cm. In this example, based on the fetal heart being at about 8.0 cm, in accordance with the dynamic windowing process (as defined via the power optimization protocol 204) the control component 202 can tailor the active portion of the Tx period to include only the portion of the Tx period occurring between about the 30$^{th}$ us time point and the 90$^{th}$ μs time point (e.g., in accordance with predefined optimal active portion criteria correlated to corresponding depths and/or in accordance with a dynamically adapting the active Tx period, as described below).

Figure 6D:
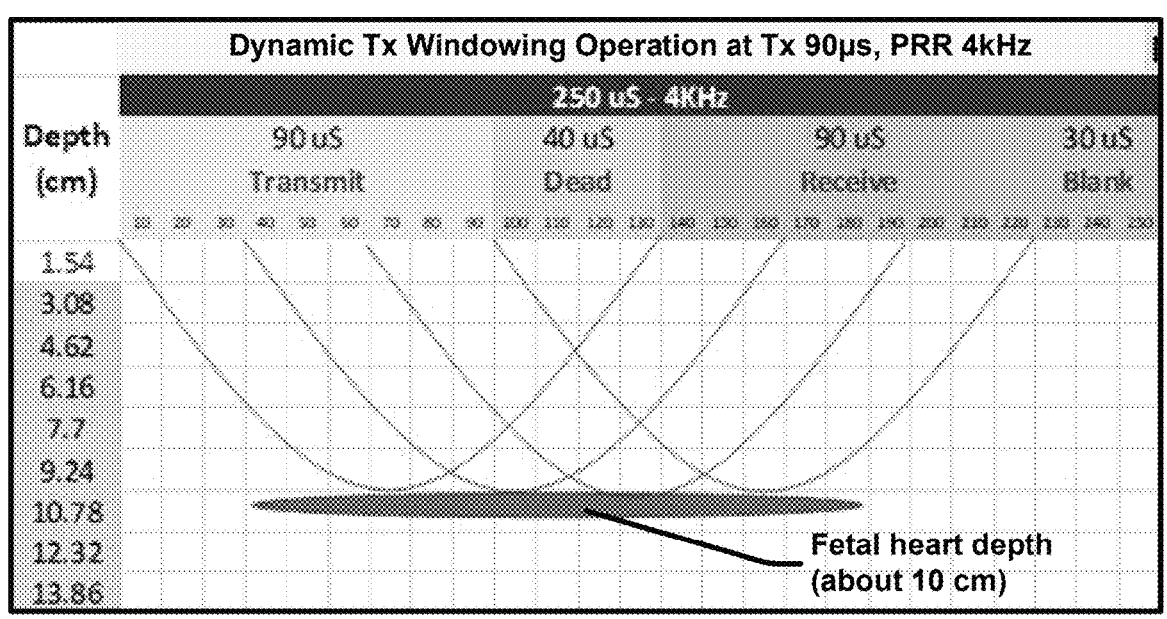

FIG. 6D presents another example chart 604 corresponding to a scenario in which the fetal heart is positioned at about 10.0 cm. In this example, based on the fetal heart being at about 10.0 cm, in accordance with the dynamic windowing process (as defined via the power optimization protocol 204) the control component 202 can tailor the active portion of the Tx period to include only the entirety of the 90 μs Tx period (e.g., in accordance with predefined optimal active portion criteria correlated to corresponding depths and/or in accordance with a dynamically adapting the active Tx period, as described below).

Of particular note, in accordance with this operating schema (e.g., a PRR of 4 kHz and the corresponding transmit, dead, receive and blank period time schema), the 10.0 cm depth is typically the only depth at which the ultrasound pulses transmitted over the entirety of the 90 μs Tx period are received during the Rx period. Thus, in some implementations, for certain depths at which all of the ultrasound signals emitted over the entirety of the fixed Tx period are received during the receive period under a particular operating schema for the ultrasound transducer), the dynamic Tx windowing protocol (e.g., as defined in the power optimization protocol 204) can direct the control component to set the active portion of the Tx period to include the entirety of the Tx period.

As can be observed via comparison of graphs 601-604, generally, the closer the fetal heart is to the FSD 104 (and/or the abdominal surface) and thus the smaller the depth, the farther the position of the active portion is located relative to the start time of the fixed Tx period. Likewise, the farther the fetal heart is from the FSD 104 (and/or the abdominal surface) and thus the greater the depth, the closer the position of the active portion is located relative to the start time of the fixed Tx period. To this end, generally and in accordance with this operating schema, the beginning of the Tx period (e.g., closer to start point) corresponds to the useful portion of the Tx period (e.g., in which the transmitted pulses are actually received during the Rx period) for depths greater than about the 10.0 cm depth (e.g., between a defined range, such as between about 11 cm and about 16 cm or another defined range), and the ending of the Tx period (e.g., closer to the end point) corresponds to the useful portion of the Tx period for depths less than about the 10.0 cm depth.

With reference briefly to FIG. 4, as shown in chart 400, under the given operating configuration (e.g., a PRR of 4 kHz and the corresponding transmit, dead, receive and blank period time schema), the lowest depth at which the first emitted ultrasound wave can reach a fetal heart and be reflected back to the ultrasound transducer during the Rx period of each duty cycle is between about 15.0 cm and 16.0 cm. To this end, for depths of about 16.0 cm or greater, any ultrasound signals emitted during any portion of the fixed 90 μs Tx period for a given duty cycle are not received during the Rx period of the given duty cycle. In some implementations of these scenarios, in order to monitor fetal hearts at depths of about 16 cm or greater, the ultrasound transducer 222 can be configured to measure the ultrasound signals as received in the Rx period of the subsequent duty cycle, as illustrated in FIG. 6E.

Figure 6E:
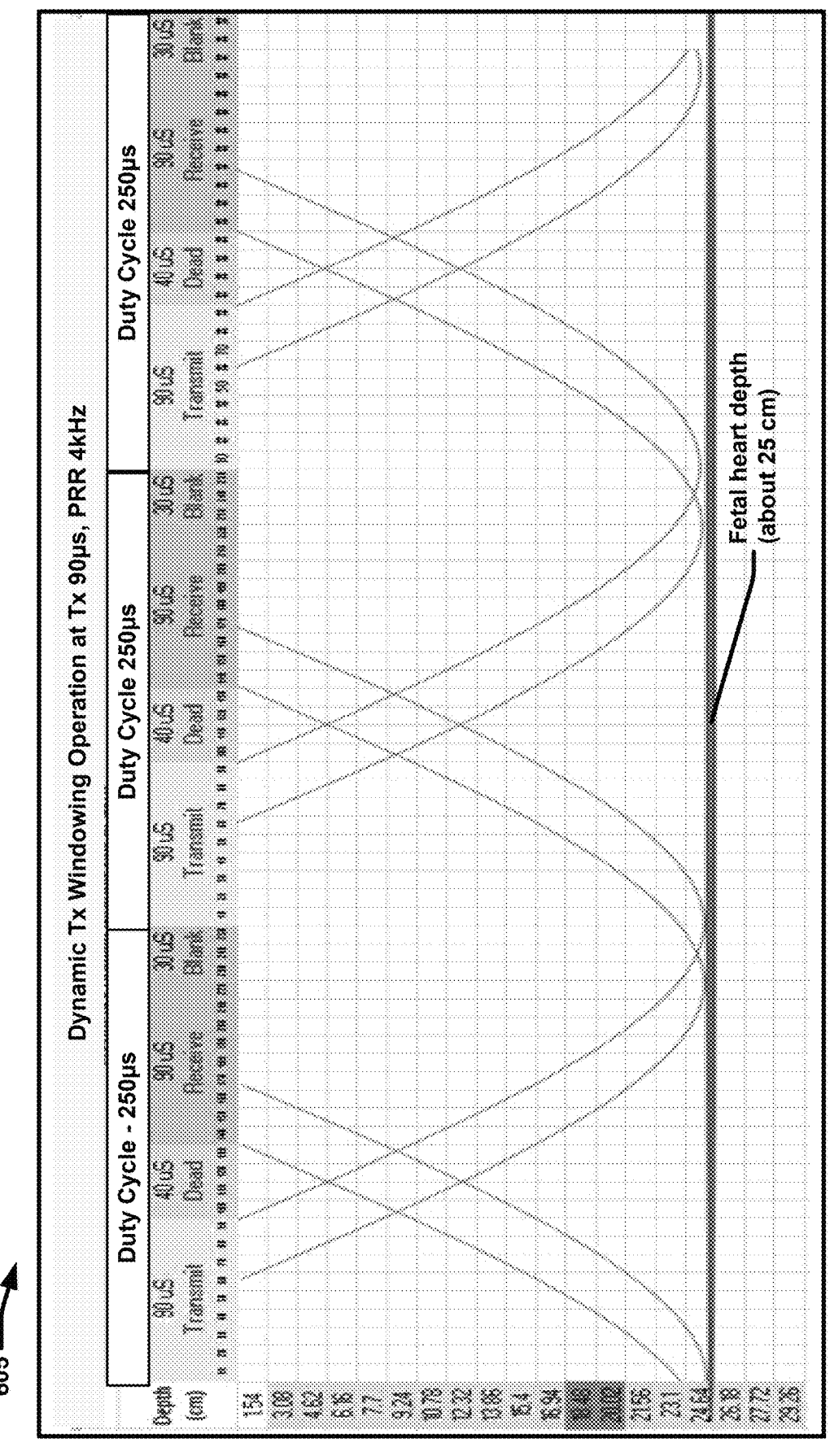

For example, FIG. 6E presents another example chart 605 corresponding to a scenario in which the fetal heart is positioned at about 25 cm. Chart 605 depicts three sequential duty cycles. Each duty cycle has the same time schema (e.g., a total duration of 250 μs with the same fixed durations for the Rx, dead, receive and bland periods). In this example, based on the fetal heart being at about 25 cm (or similar depths greater than about 16 cm), a relatively large depth, the duration of time required for the ultrasound signals to reach the heart and be reflected back to the ultrasound transducer is typically longer than the 250 μs timeframe employed for a single duty cycle in accordance with the given operating configuration. With these implementations, some of the reflected ultrasound signals emitted during the Tx period of an immediate duty cycle can be received during the Rx period of the subsequent duty cycle, as shown in FIG. 6E. With these embodiments, based on the fetal heart being at depths beyond about 16 cm, the control component 202 can configure the active portion of the fixed Tx period to result in transmission of ultrasound pulses that will be received in the Rx period of the subsequent duty cycle, as shown in FIG. 6E. In accordance with this example, this corresponds to the active portion including the ending of the Tx period between about the 60$^{th}$ and the 90$^{th}$ μs time points (e.g., in accordance with predefined optimal active portion criteria correlated to corresponding depths and/or in accordance with dynamically adapting the active Tx period, as described below). With these implementations, based on the fetal heart being known to be greater than a defined depth (e.g., 16 cm or another threshold depth in which the emitted signals are received in the subsequent Rx period following the immediate Tx period), the signal processing component 206 will know (or can be configured to assume) the reflected signals received during each Rx period correspond to reflections of ultrasound signals transmitted in the immediately preceding duty cycle of each Rx period.

To this end, if the depth of the fetal heart is unknown, the signal processing component 206 will not know whether the reflected waves received during an Rx period of a given duty cycle were emitted during the given duty cycle or the immediately preceding duty cycle to the given duty cycle. Accordingly, the depth estimation component 208 cannot differentiate between a fetal heart corresponding to a relatively shallow depth (e.g., 5.0 cm) attributed to reflected signals received in the beginning of the Rx period of a given duty cycle that were transmitted in the given duty cycle, and a fetal heart corresponding to a relatively deep depth (e.g., 25 cm) attributed to signals received in the Rx period that were transmitted in the immediately preceding duty cycle.

To mitigate this issue, in some implementations of these embodiments, the control component 202 can configure the ultrasound transducer 222 to initially operate in a calibration mode using alternating duty cycles involving a normal duty cycle (e.g., involving the normal Tx, dead, Rx and blank period sequence) followed by a wait period having the same duration as the normal duty cycle, wherein during the wait period the ultrasound transducer does not transmit or receive. For instance, in accordance with the example configurations illustrated in FIG. 6E in which the normal duty cycle is 250 µs, the wait period would also be 250 µs, thus effectively operating the ultrasound transducer 222 at 2.0 kHz but only receiving for a 90 µs Rx period. With these implementations, the FSD can determine (e.g., via depth estimation component 208) whether the fetal heart is less than or greater than a defined depth threshold (e.g., 16 cm, 25 cm or another defined depth threshold tailored based on the operating configuration of the ultrasound transducer 222) based on whether any signals of interest are received during the Rx periods of the normal duty cycle. In this regard, if the fetal heart is at a position less than the defined depth threshold, reflected ultrasound signals of interest (e.g., reflections from the fetal heart as opposed to noise signals) will be received during each Rx period of the normal duty cycles. However, if the fetal heart is at a position greater than the depth threshold, no Rx signals of interest will be received during each Rx period of the normal duty cycles. In this regard, in association with measuring the received signals, the signal processing component 206 can also determine the SNR of the received signals to quantify the signals of interest, wherein a high SNR (e.g., relative to one or more defined threshold) indicates strong signals of interest as opposed to a low SNR. In this manner, the depth estimation component 208 can determine whether the depth of the fetal heart corresponds to a depth less than the depth threshold (e.g., based on reception of signals of interest during the Rx periods, as determined based on their SNR being higher than a defined SNR threshold) or greater than the depth threshold (e.g., based on no reception of signals or reception of only noise signals as indicated by the signals having a low SNR relative to a defined SNR threshold). Once the this has been determined, the control component 202 can reconfigure the ultrasound transducer to operate in accordance with the normal active mode (e.g., with sequential duty cycles) and optimize the active portion of the Tx periods using the techniques described herein.

It should be appreciated that the depths and corresponding active portions of the Tx periods illustrated in FIGS. 6A-6E in accordance with the adaptive Tx windowing process are merely exemplary. In this regard, the actual optimal active portions of the Tx period over which the ultrasound transducer 222 only transmits ultrasound signals that are reflected by a targeted fetal heart and received during the Rx period will vary not only based on the depth of the fetal heart but other factors unique to each usage scenario (e.g., the PRR, the transmission power, other operating/configuration parameters of the ultrasound transducer 222, the SNR values, the anatomy of the mother, and so on), and can vary over the course of the monitoring session.

Figure 7A:
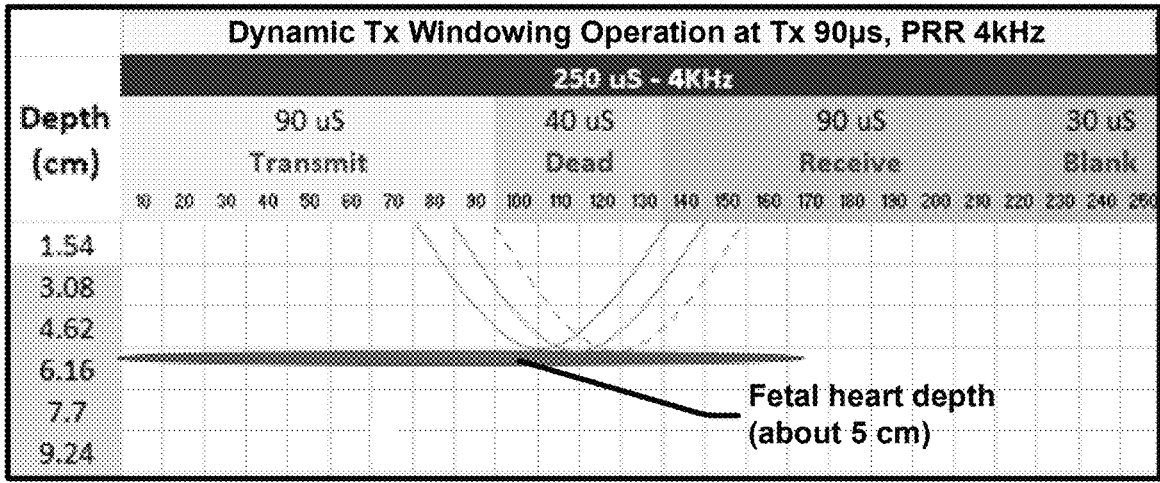
FIGS. 7A and 7B present charts illustrating different example configurations for further deducing the active portion of the Tx period, in accordance with one or more embodiments of a dynamic windowing process.
Figure 7B:
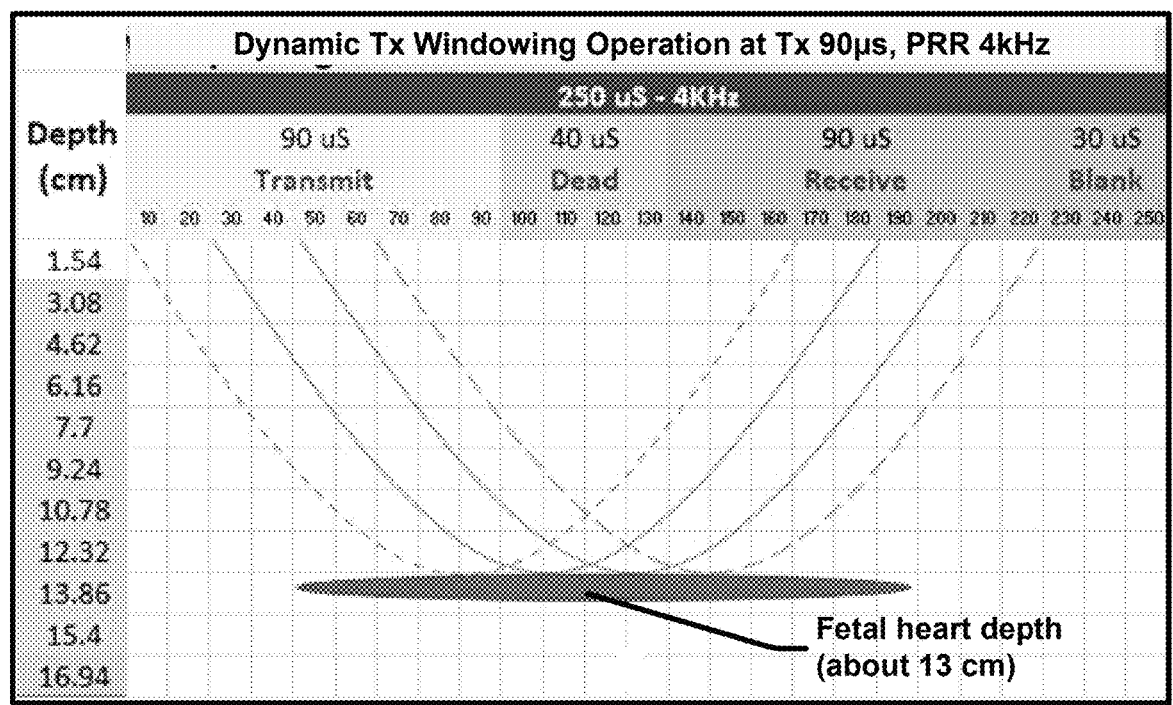

In addition, in some embodiments, the control component 202 can further reduce the duration of the active portion within the optimal timeframe of an active portion tailored based on the depth of the fetal heart (e.g., wherein the optimal timeframe corresponds to the optimal start and end time of the active portion within the fixed, first duration of the Tx period) to further reduce the duration of the active portion and minimize power consumption, as illustrated in FIGS. 7A and 7B. In this regard, FIGS. 7A and 7B respectively present charts 701 and 702 corresponding to charts 601 and 602 yet with even further reduced active portions. In these examples, the dashed parabolas correspond to ultrasound signals that can be omitted from transmission during the active portion, effectively further reducing the duration of the active portion and associated power consumption. For example, as applied to the 5.0 cm scenario, the duration of the active portion in this example can be further reduced to include only the portion of the Tx period occurring between the $70^{th}$ and $80^{th}$ µs time points (excluding the previous active portion occurring between the $80^{th}$ and $90^{th}$ time points illustrated in chart 601). Similarly, as applied to the 13.0 cm scenario, the duration of the active portion in this example can be further reduced to include only the portion of the Tx period occurring between the $20^{th}$ and $60^{th}$ µs time points (excluding the previous active portion occurring on either sides thereof, that is between the 0 and $20^{th}$ us time points and between the between the $60^{th}$ and $70^{th}$ µs time points.

With these embodiments, the power optimization protocol 204 can direct the control component 202 to further reduce the duration and/or position of the active portion as exemplified in FIGS. 7A and 7B, based on the SNR value or values associated with the received signals being high (e.g., relative to a defined threshold) and/or the SNR values received over a defined timeframe increasing or consistently remaining high (e.g., relative to one or more defined thresholds). To this end, when the SNR values are high, this indicates strong/good signal quality and thus fewer instances of the received signals can be used to accurately detect and calculate the corresponding FHR (e.g. via the signal processing component 206). Thus, the SNR value or values can be used as a process variable (e.g., in the power optimization protocol) to control the duration and position of the active window of the Tx period.

In this regard, in some embodiments, after the active portion of the Tx period has been determined and applied, the dynamic Tx windowing process can direct the control component 202 to continuously monitor the SNR values of the received signals and further adapt the duration and/or position of active portion based on the SNR values. For example, the power optimization protocol 204 can direct the control component 202 to incrementally decrease the duration of the active portion relative to the optimal duration/position defined and/or determined for a corresponding fetal heart depth so long as the FHR values calculated based thereon are acceptable (e.g., relative to consistency and/or range) and until the minimum SNR threshold is reached, in accordance with a similar process to process 300, with the difference being adjusting the duration and/or position of the active portion as opposed to (or in addition to) the transmission power. This can correspond to further narrowing the duration of the active portion on the left and/or right sides thereof. For example, in some implementations, the power optimization protocol 204 can direct the control component to incrementally decrease the duration of the active portion by moving the start point of the active portion away from the fixed start point of the Tx period and moving the end point the active portion toward the fixed start point, as shown in graph 702. In other implementations, the power optimization protocol 204 can direct the control component to incrementally decrease the duration of the active portion by moving either the start point of the active portion away from the fixed start point of the Tx period, or moving the end point the active portion toward the fixed start point, as shown in graph 701. In some implementations, the direction of movement can be dynamically determined based on monitored changes to the SNR values (e.g., wherein a significant drop indicates the wrong direction) and/or based predetermined as correlated to known fetal depths and corresponding optimal active portion settings for a given operating configuration.

In most scenarios, the depth or position of the fetal heart may not be known by the control component 202 at the beginning and/or initiation of the fetal monitoring session and may change over the course of the fetal monitoring session. In this regard, in some embodiments in which the fetal depth or estimated fetal depth is known, the power optimization protocol 204 can define recommended optimal active portions of the Tx period (e.g., with respect to duration and position relative to the start and end points of the fixed Tx period) for configuring the ultrasound transducer 222, wherein the recommended active portions correspond to different fetal depths and optionally other variables. In some implementations of these embodiments, the control component 202 can apply the recommended active portions in scenarios in which the depth of the targeted fetal heart is known and thereafter adjust them accordingly thereafter based on the monitored SNR and the corresponding FHR values, as described with reference to FIGS. 7A-7B and further described below.

In various embodiments in which the depth of the fetal heart is unknown, the depth estimation component 208 can estimate the depth of the fetal heart based on monitored changes to the SNR values of the received signals over time in association with adapting the active portion of the Tx period. For example, the dynamic Tx windowing protocol can direct the control component 202 to dynamically adjust (e.g., decrease and/or increase) the duration of the active portion and/or dynamically move the position of the active portion towards and/or away from the start point of the fixed duration while monitoring the corresponding SNR values of the received signals and/or the number of the signals received during the Rx period. The depth estimation component 208 can further estimate the depth of the fetal heart based on how the changes influence the SNR values (e.g., either decreasing or increasing the SNR values) and previously correlated relationships between the different defined active portions (e.g., with respect to duration and position within the fixed Tx period) and corresponding depths.

For example, in some embodiments, at the initiation of the fetal monitoring session and/or in other scenarios in which the depth of the fetal heart is unknown (e.g., in association with repositioning the FSD or another scenario), the control component 202 can be configured to set the active portion of the fixed Tx period to a default active portion, such as the entirety of the fixed Tx period. Thereafter, the control component 202 can dynamically adjust the default active portion while monitoring how the adjustments change the SNR of the received signals over time and/or the corresponding FHR values determined based on the received signals. For example, the dynamically adjusting can include decreasing the duration of the default active portion in association with moving the start time and end time of the active portion away from and/or towards the fixed start time of the fixed Tx period. With these embodiments, a decrease to the SNR and/or the resulting FHR values corresponding to unacceptable (or missing) values corresponds to an adjustment or movement in the wrong direction. Likewise, an increase to the SNR and/or resulting FHR values corresponding to acceptable or even more preferable (e.g., with respect to consistency and/or value BMP value range) corresponds to an adjustment or movement in the right direction.

Thus, in some embodiments the control component 202 can dynamically adjust the default active portion in a manner that results in the received signals satisfying defined optimization criteria for the SNR of the signals over time and/or the FHR values determined based on the received signals (e.g., defined acceptable criteria for the FHR values discussed above with reference to FIG. 4 and process 400). In some implementations the defined optimization criteria can include or correspond to achieving or maintaining the highest observered SNR value and/or achieving and/or maintaining a stable SNR value or value within an acceptable SNR value range). For example, the control component 202 can dynamically decrease and/or increase the duration of the active portion and/or change the position of the active portion while monitoring the SNR values resulting from the respective changes. The control component 202 can further determine the optimal duration and/or position for the active portion that results in the SNR values remaining or becoming high (e.g., relative to one or more thresholds) and/or remaining or become consistently acceptable (e.g., relative a defined optimal value or range). In this regard, the control component 202 can dynamically adjust the active portion while monitoring the SNR of the received signals and/or the resulting FHR values over time until an optimal active portion is identified that results in satisfying defined optimization criteria for the SNR of the signal (e.g., the SNR values being above a threshold, the SNR values consistently remaining within a defined threshold range, and/or maximizing the SNR values of the received signals) and/or achieving acceptable FHR values (e.g., with respect to defined FHR value acceptability criteria). The control component 202 can further set the active portion to the resulting optimal active portion determined based on adjusting the default active portion in accordance with the dynamically adjusting process described above.

The depth estimation component 208 can further estimate the depth of the fetal heart based on the resulting active portion and previously determined information correlating different optimal active portions for the given operating configuration to corresponding fetal depths (e.g., those illustrated in FIGS. 6A-6E for example). Additionally, or alternatively, as described with reference to FIGS. 6A-6E, generally, the closer the fetal heart is to the FSD 104 (and/or the abdominal surface) and thus the smaller the depth, the farther the position of the active portion is located relative to the start time of the fixed Tx period. Likewise, the farther the fetal heart is from the FSD 104 (and/or the abdominal surface) and thus the greater the depth, the closer the position of the active portion is located relative to the start time of the fixed Tx period (e.g., unless the fetal heart is greater than 16 cm, 20 cm, or another defined depth, as described with reference to FIG. 6E). Thus, in other embodiments, the depth estimation component 208 can employ a depth estimation algorithm that accounts for this realization in association with estimating the depth of the fetal heart based on position and duration of the resulting active Tx period. For example, the depth detection algorithm can correlate the position (e.g., with respect to the start and end times of the active portion within the fixed Tx period) and duration of the active portion to a corresponding fetal depth using a function that decreases the resulting depth estimation as the position of the active portion becomes farther away from the fixed start point of the fixed Tx period and increases the depth estimation as the position of the active portion becomes closer to the fixed start point of the fixed Tx period.

For example, in association with moving the active portion away from the start point of the fixed duration of the Tx period and observing the SNR values remaining unchanged (e.g., remaining the same or within the same range) and/or increasing, the depth estimation algorithm employed by the depth estimation component 208 can determine that the depth of the fetal heart is relatively shallow (e.g., less than about 10 cm) and/or at a corresponding previously correlated shallow depth value to the final resulting active portion. For example, if we start with a default active portion comprising the entirety of the fixed Tx period and the fetal heart is at about 5.0 cm, the moving the active portion away from the start point of the fixed Tx period (e.g., decreasing the duration of the active portion from the left to the right), the SNR should remain the same or substantially the same until we reach about the $70^{th}$ µs time point. After that, the SNR will drop. That indicates the depth of the heart corresponding to the 5.0 cm depth. Similarly, if the heart is at 8.0 cm, once the active portion start point moves to roughly 30 µs, we will see a reduction in the SNR. That again tells us the depth. Additionally, in some implementations, by decreasing the active transmission of signals in association with decreasing the duration of the active portion (e.g., stopping transmission of signals between the 0-$70^{th}$ µs time points of the fixed Tx period for the 5 cm example), this minimizes the amount of noise signals received during the Rx period (e.g., reflected signals from other tissues, and other sources of noise). As a result, the SNR of the received signals may actually increase initially as the active portion is decreased until the optimal start point of the active portion is passed (e.g., until the $70^{th}$ µs time point is passed in the 5.0 cm example).

Likewise, in association with moving the active portion toward the start point of the fixed duration of the Tx period and observing the SNR values remaining unchanged (e.g., remaining the same or within the same range) and/or increasing, the depth estimation algorithm employed by the depth estimation component 208 can determine that the depth of the fetal heart is relatively deep (e.g., greater than about 10 cm) and/or at a corresponding previously correlated deep depth value to the final resulting active portion. For example, if the heart is at a depth of more than 10 cm, say for example 13 cm, and using a default active portion corresponding to the entirety of the fixed Tx period, then moving the start point of the active portion even a bit away from the fixed start time of the fixed Tx period (e.g., decreasing the active portion from the left to the right) will cause the SNR of the received signals to decrease. In that case, the control component 202 can dynamically reset the default active portion and try moving the end point of the active portion towards the fixed start time of the fixed Tx period (e.g., decreasing the duration of the active portion from the right to the left) until the SNR begins to decrease. For instance, in accordance with the example shown in FIG. 6B, for the 13 cm scenario, the drop in SNR would be observed after moving the end point of the active portion past the $60^{th}$ µs mark in the direction toward the start point of the fixed Tx period, thereby indicating the corresponding depth of the fetal heart being at about 13 cm.

In another example, in association with adjusting the duration and/or position of the active portion for a fetal heart determined to be at a depth greater than a defined depth threshold (e.g., 16 cm or another defined depth threshold), the control component 202 can also dynamically adjust the active portion of the Tx period in these scenarios in the same manner described above in association with finding the optimal active portion for these deeper depths and estimating the actual depth of the fetal heart (e.g., a depth between 16 cm and the deepest detectable depth).

With these embodiments, once the active portion of the Tx period has been set, the control component 202 can continuously monitor the SNR values of the received signals, and based on a reduction/increase in SNR, the control component 202 can adapt the position of active portion towards/away from the start point of the fixed duration of the Tx period and/or adapt the duration of the active portion, accordingly in a manner that results in optimizing the active portion over the course of the monitoring session while accounting for changes to the fetal depth/position over the course of the monitoring session. In addition, by dynamically adapting the active portion in this manner, the depth estimation component 208 can track the position of the fetal heart as it moves towards or away from the ultrasound transducer 222 over the course of the monitoring session. To this end, in some embodiments, the depth estimation component 208 can estimate and track changes to the depth of the heart of the fetus within the womb 106 in association with moving the position of the active region based on changes to the SNR values over time.

The depth estimation and dynamic Tx windowing also minimizes the undesirable detection of artifacts by the ultrasound transducer 222, such as the maternal heart rate (MHR) and other potential artifacts.

In some embodiments, in addition to the one or more active mode power optimization processes, the power optimization protocol 204 can also define a power optimization protocol that involves automatically switching the FSD between the active mode and a sleep mode based on the usage status of the FSD. In this regard, the ultrasound FSD 104 can be configured to operate in a sleep mode wherein the ultrasound transducer deactivates transmission of at least some ultrasound pulses, thereby conserving power when the FSD is not in use for an active monitoring session. For example, as applied to wireless FSDs, in many clinical contexts, the FSDs are often used for a monitoring session and accidentally left turned on (e.g., in the active mode) after the session, thereby draining their power rendering them not available for usage for another monitoring session until their batteries have been recharged or replaced.

With this context in mind, the power optimization protocol 204 can define a sleep mode for the FSD in which the transmission of ultrasound signals by the ultrasound transducer 222 is deactivated or substantially deactivated (e.g., via the control component 202) when the FSD not in use, thus significantly minimizing power consumption, with automated switching between the sleep mode and the active sensing mode. For example, the FSD can be configured with a smart turn on feature that detects the instance of the FSD being placed on the mother belly and/or the FSD being touched/repositioned by the clinician and activates the active mode. Likewise, based on detection of the FSD being no longer used for an active monitoring session, such as being removed from a mother's belly for longer than a defined idle period (e.g., 1.0 minute, 3.0 minutes, or another defined time period), the control component can automatically switch the operating mode of the FSD 104 to the sleep mode.

To facilitate this end, the power optimization protocol 204 can define an active usage status for the FSD, corresponding to the FSD being actively used for a monitoring session, and an inactive usage status corresponding to the FSD not being actively used for a monitoring session. The usage status detection component 210 can further monitor and determine whether the current usage status of FSD comprises the active usage status or the inactive usage status, and the control component 202 can activate the active mode and deactivate the sleep mode based on the usage status being the active usage status and activate the sleep mode and deactivate the active mode based on the usage status being the inactive usage status.

Techniques for determining whether the usage status of the FSD corresponds to the active usage status and the inactive usage status by the usage status detection component 210 can vary. For example, in some embodiments, the usage status detection component 210 can determine whether the usage status corresponds to the active usage status or the inactive usage status based on sensory information captured via the one or more sensors 220 and information defined in the power optimization protocol 204 correlating the sensory information with the corresponding usages statuses. For instance, in some implementations, based on sensory information captured via the one or more sensors 220, the usage status detection component 210 can determine that the usage status corresponds to the active usage or the inactive usage status based on the detecting whether the FSD is contacting the mother's skin and/or being held by a clinician or another person (e.g., using contact sensors, proximity sensors, impedance sensors, motion sensors and/or the like).

Additionally, or alternatively, in some embodiments, during active mode the usage status detection component 210 can monitor the transmit pulse voltages and predict the acoustic impedance based on changes to the pulse voltage, wherein higher transmit pulse voltages correspond to higher acoustic impedance and thus indicative of the FSD being positioned away (and/or not contacting) the mother's skin (and thus corresponding to the inactive mode). In this regard, the usage status detection component 210 can determine whether the usage status comprises the active usage status or the inactive usage status based on monitored changes to the acoustic impedance associated with the ultrasound transducer 222 as determined based on monitored changes to a voltage level of the transmitted ultrasound signals. For example, an increase in the Tx voltage can occur when the acoustic impedance increases as a result of removal of the transducer from the mother's skin. Thus, the usage status detection component 210 can determine a change from the active usage status to the inactive usage status based on significant increase to the Tx voltage (e.g., relative to a defined threshold). Likewise, the usage status detection component 210 can determine a change from the inactive usage status to the active usage status based on significant decrease to the Tx voltage (e.g., relative to the defined threshold).

In another embodiment, during the sleep mode, the FSD can be configured to periodically activate the ultrasound transducer and transmit one or more ultrasound pulses in accordance with a defined pulse pattern. The usage status detection component 210 can further monitor the voltage of the one or more transmitted pulses during the sleep mode in association with detecting a drop in voltage. For example, a drop in the Tx voltage can occur when the acoustic impedance falls as a result of placement of the transducer on the mother's skin. Thus, based on detection of a drop in the voltage during sleep mode (e.g., via the usage status detection component 210), the control component 202 can automatically deactivate the sleep mode and activate the active mode of the FSD 104. Additionally, or alternatively, the usage status detection component 210 can perform a skin impedance check using embedded electrodes on the bottom surface of the FSD to determine and/or verify if the transducer is placed on the mother's skin or not.

Very often, during an active monitoring session with movement of the fetus away from the line of sight of the transducer, the FHR signal is lost and the caregiver has to reposition the FSD. In some implementations of these scenarios, the control component 202 can temporarily activate the sleep mode of the FSD 104 to conserve power while the FSD remains in the same position on the mother's belly. The usage status detection component 208 can further determine when the FSD is being repositioned based on contact between the FSD and the clinician (e.g., using one or more context sensors, proximity sensors, motion sensors, etc.) and then switch the FSD back to the active mode.

FIG. 8 illustrates a block diagram of an example, non-limiting computer implemented method 800 that facilitates reducing power consumption by a FSD, in accordance with one or more embodiments of the disclosed subject matter. Method 800 comprises controlling (e.g., via control component 202), by a FSD comprising a processor (e.g., FSD 104), operations of an ultrasound transducer (e.g., ultrasound transducer 222) of the FSD in accordance with a power optimization protocol that results in minimizing power consumption by the FSD, wherein the ultrasound transducer is configured to measure signals representative of one or more fetal parameters of a fetus using doppler based ultrasound technology in association with positioning of the FSD on an external body of a mother of the fetus, wherein the FSD operates in an active mode that comprises alternating between transmit periods wherein the ultrasound transducer transmits ultrasound signals, and receive periods wherein the ultrasound transducer measures reflected signals of the ultrasound signals that are received by the ultrasound transducer during the receive periods, and wherein the controlling comprises controlling at least one of a transmission power of the ultrasound signals or a duration of the transmit periods during the active mode in accordance with the power optimization protocol (e.g., power optimization protocol 204).

In various embodiments, the controlling comprises adjusting, by the FSD during the active mode, at least one of the transmission power or the duration of the transmit periods based on a SNR of the reflected signals of the ultrasound signals and/or based on a depth of a heart of the fetus within the womb (e.g., wherein the depth corresponds to the distance between the FSD 104, as positioned on the external body of the mother, and the fetal heart, as positioned within the womb of the mother). For example, in some embodiments, the controlling comprises performing, during the active mode, a transmission power optimization process (e.g., transmission optimization process 300) defined by the power optimization protocol 204.

Additionally, or alternatively, the controlling comprises performing, during the active mode, a dynamic Tx windowing process (e.g., as defined by the power optimization protocol 204). As described with reference to FIGS. 5A-7B, in some embodiments of the dynamic Tx windowing process, the Tx periods are constrained by a first duration (e.g., 90 microseconds in the examples shown or another constrained duration) defined by a start time and end time, wherein the duration of the transmit periods associated with the controlling comprises a second duration within the first duration, the second duration corresponding to the active portion of the fixed Tx period (e.g., wherein the ultrasound transducer only transmit the ultrasound signals during the active portion), and wherein the controlling comprises adjusting a duration of the active portion within the first duration and/or a position of the active portion relative to the start time and the end time in accordance with a dynamic Tx windowing protocol defined in the power optimization protocol 204. Additionally, or alternatively, the controlling can comprise switching operation of the FSD between the active mode and sleep mode based on the usage status of the FSD corresponding to an active usage status and an inactive usage status, respectively (e.g., as determined by the usage status detection component 210).

FIG. 9 illustrates a block diagram of another example, non-limiting computer implemented method 900 that facilitates reducing power consumption by a FSD, in accordance with one or more embodiments of the disclosed subject matter. Method 900 corresponds to an adaptive Tx windowing process in accordance with one or more embodiments. In this regard, at 902 method 900 comprises activating (e.g., via control component 202), by a FSD comprising a processor (e.g., FSD 104), an active mode of the FSD, wherein the active mode comprises alternating between transmit periods wherein an ultrasound transducer of the FSD transmits ultrasound signals, and receive periods wherein the ultrasound transducer measures reflected signals of the ultrasound signals that are received by the ultrasound transducer during the receive periods. At 904, method 900 further comprises, adjusting by the FSD (e.g., via control component 202), a duration of the transmit periods during the active mode based on a SNR value of the reflected signals of the ultrasound signals and/or a depth of the fetus in accordance with a power optimization component that facilities minimizing power consumption by the FSD (e.g., power optimization protocol 204).

For example, in some embodiments, the adjusting can comprise decreasing the duration of the active portion of transmit periods based on observing no or minimal change (e.g., relative to a defined degree of deviation) to the SNR value or values of the received signals and/or an increase to the SNR value or values, and increasing the duration of the active portion of the transmit periods based on observing a decrease to the SNR value or values. In other embodiments, the adjusting can include finding the optimal active portion and setting the active portion to the optimal active portion (e.g., optimal duration and position). As describe above, this can involve adjusting, by the FSD (e.g., via control component 202), the duration and/or position of the active portion from a default duration and/or position (e.g., the entirety of the fixed Tx period or another default setting), monitoring, by the FSD, changes to the SNR of the reflected signals of the ultrasound signals in association with the adjusting, and setting, by the FSD, second duration and/or the position of the active portion to an optimal duration and/or optimal position based on the SNR of the reflected signals of the ultrasound signals received at the optimal duration and/or optimal position satisfying defined SNR optimization criteria.

Still in other embodiments in which the optimal active portion has already been determined and set, the adjusting at 904 can include or correspond to further adjusting the optimal active portion, as described with reference to FIGS. 7A and 7B. Additionally, or alternatively, in other embodiments in which the optimal active portion has already been determined and set, the adjusting at 904 can include or correspond to further adjusting the optimal active portion based on monitored changes to the SNR and/or based on the SNR values no longer satisfying the SNR optimization criteria (e.g., based on movement of the fetus over the course of the monitoring session and/or other factors). This process can include or correspond to continuously determining and adjusting the optimal active portion over the course of the monitoring session based on changes to the SNR over time.

FIG. 10 illustrates a block diagram of another example, non-limiting computer implemented method 1000 that facilitates reducing power consumption by a FSD and estimating fetal depth, in accordance with one or more embodiments of the disclosed subject matter. Method 1000 corresponds to another adaptive Tx windowing process, in accordance with one or more embodiments. In this regard, at

1002 method 1000 activating (e.g., via control component 202), by a FSD comprising a processor (e.g., FSD 104), an active mode of the FSD, wherein the active mode comprises alternating between transmit periods wherein an ultrasound transducer of the FSD transmits ultrasound signals, and receive periods wherein the ultrasound transducer measures reflected signals of the ultrasound signals that are received by the ultrasound transducer during the receive periods, and wherein the transmit periods are constrained by a fixed duration defined by a start time and an end time. At 1004, method 1000 further comprises, adjusting by the FSD, a duration and/or position of the active portion of the transmit periods in association with configuring the ultrasound transducer to only transmits the ultrasound signals during the active portion (e.g., via control component 202). At 1006, method 1000 comprise monitoring, by the FSD, changes to a SNR associated with the reflected signals of the ultrasound signals in association with the adjusting (e.g., via control component 202). At 1008, method 1000 comprise estimating, by the FSD, a depth of the heart of the fetus based on the changes in association with the adjusting (e.g., via depth estimation component 208).

FIG. 11 illustrates a block diagram of another example, non-limiting computer implemented method 1100 that facilitates reducing power consumption by a FSD, in accordance with one or more embodiments of the disclosed subject matter. Method 1100 comprises at 1102, monitoring, by an FSD comprising a processor (e.g., FSD 104), a usage status of the FSD (e.g., via usage status detection component 210). At 1104, method 1100 comprises activating, by the FSD (e.g., via control component 202), an active mode of the FSD based on the usage status corresponding to an active usage status. At 1106, method 1100 comprises, deactivating, by the FSD, the active mode and activating a sleep mode of the FSD based on the usage status corresponding to an inactive usage status (e.g., via the control component 202).

Example Operating Environments

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire. To this end, a computer readable storage medium, a machine-readable storage medium, or the like as used herein can include a non-transitory computer readable storage medium, a non-transitory machine-readable storage medium, and the like.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 12, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 12:
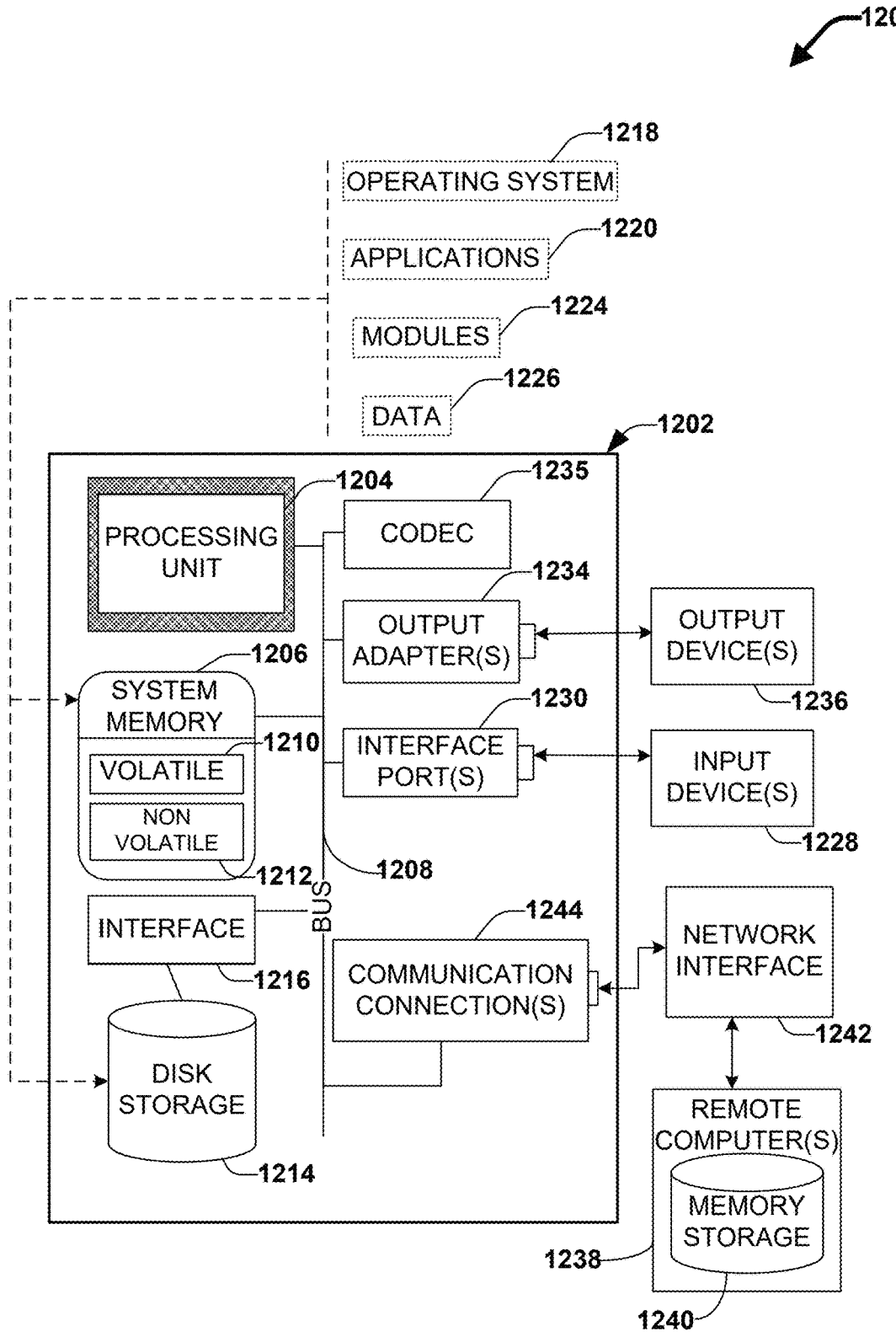
FIG. 12 illustrates a block diagram of an example, non-limiting operating environment in which one or more embodiments described herein can be facilitated.

With reference to FIG. 12, an example environment 1200 for implementing various aspects of the claimed subject matter includes a computer 1202. The computer 1202 includes a processing unit 1204, a system memory 1206, a codec 1235, and a system bus 1208. The system bus 1208 couples system components including, but not limited to, the system memory 1206 to the processing unit 1204. The processing unit 1204 can be any of various available processors. Dual microprocessors and other multiprocessor architectures also can be employed as the processing unit 1204.

The system bus 1208 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13124), and Small Computer Systems Interface (SCSI).

The system memory 1206 includes volatile memory 1210 and non-volatile memory 1212, which can employ one or more of the disclosed memory architectures, in various embodiments. The basic input/output system (BIOS), containing the basic routines to transfer information between elements within the computer 1202, such as during start-up, is stored in non-volatile memory 1212. In addition, according to present innovations, codec 1235 can include at least one of an encoder or decoder, wherein the at least one of an encoder or decoder can consist of hardware, software, or a combination of hardware and software. Although, codec 1235 is depicted as a separate component, codec 1235 can be contained within non-volatile memory 1212. By way of illustration, and not limitation, non-volatile memory 1212 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1212 can employ one or more of the disclosed memory devices, in at least some embodiments. Moreover, non-volatile memory 1212 can be computer memory (e.g., physically integrated with computer 1202 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1210 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1202 can also include removable/non-removable, volatile/non-volatile computer storage medium. FIG. 12 illustrates, for example, disk storage 1214. Disk storage 1214 includes, but is not limited to, devices like a magnetic disk drive, solid state disk (SSD), flash memory card, or memory stick. In addition, disk storage 1214 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1214 to the system bus 1208, a removable or non-removable interface is typically used, such as interface 1216. It is appreciated that disk storage 1214 can store information related to a user. Such information might be stored at or provided to a server or to an application running on a user device. In one embodiment, the user can be notified (e.g., by way of output device(s) 1236) of the types of information that are stored to disk storage 1214 or transmitted to the server or application. The user can be provided the opportunity to opt-in or opt-out of having such information collected or shared with the server or application (e.g., by way of input from input device(s) 1228).

It is to be appreciated that FIG. 12 describes software that acts as an intermediary between users and the basic computer resources described in the suitable operating environment 1200. Such software includes an operating system

1210. Operating system 1210, which can be stored on disk storage 1214, acts to control and allocate resources of the computer 1202. Applications 1220 take advantage of the management of resources by operating system 1210 through program modules 1224, and program data 1226, such as the boot/shutdown transaction table and the like, stored either in system memory 1206 or on disk storage 1214. It is to be appreciated that the claimed subject matter can be implemented with various operating systems or combinations of operating systems.

A user enters commands or information into the computer 1202 through input device(s) 1228. Input devices 1228 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1204 through the system bus 1208 via interface port(s) 1230. Interface port(s) 1230 include, for example, a serial port, a parallel port, a game port, and a universal serial bus (USB). Output device(s) 1236 use some of the same type of ports as input device(s) 1228. Thus, for example, a USB port can be used to provide input to computer 1202 and to output information from computer 1202 to an output device 1236. Output adapter 1234 is provided to illustrate that there are some output devices 1236 like monitors, speakers, and printers, among other output devices 1236, which require special adapters. The output adapters 1234 include, by way of illustration and not limitation, video and sound cards that provide a means of connection between the output device 1236 and the system bus 1208. It should be noted that other devices or systems of devices provide both input and output capabilities such as remote computer(s) 1238.

Computer 1202 can operate in a networked environment using logical connections to one or more remote computers, such as remote computer(s) 1238. The remote computer(s) 1238 can be a personal computer, a server, a router, a network PC, a workstation, a microprocessor based appliance, a peer device, a smart phone, a tablet, or other network node, and typically includes many of the elements described relative to computer 1202. For purposes of brevity, only a memory storage device 1240 is illustrated with remote computer(s) 1238. Remote computer(s) 1238 is logically connected to computer 1202 through a network interface 1242 and then connected via communication connection(s) 1244. Network interface 1242 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1244 refers to the hardware/software employed to connect the network interface 1242 to the bus 1208. While communication connection 1244 is shown for illustrative clarity inside computer 1202, it can also be external to computer 1202. The hardware/software necessary for connection to the network interface 1242 includes, for exemplary purposes only, internal and external technologies such as, modems including regular telephone grade modems, cable modems and DSL modems, ISDN adapters, and wired and wireless Ethernet cards, hubs, and routers.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SL-DRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A fetal sensor device (FSD), comprising:
an ultrasound transducer configured to measure signals representative of one or more fetal parameters of a fetus using doppler based ultrasound technology in association with positioning of the FSD on an external body of a mother of the fetus, wherein the FSD operates in an active mode that comprises alternating between transmit periods wherein the ultrasound transducer transmits ultrasound signals, and receive periods wherein the ultrasound transducer measures reflected signals of the ultrasound signals that are received by the ultrasound transducer during the receive periods;

at least one memory that stores computer-executable components; and
at least one processor that executes the computer-executable components stored in the at least one memory, wherein the computer-executable components comprise:
a control component that controls, while maintaining operation of the ultrasound transducer in the active mode, at least one of a transmission power of the ultrasound signals or a duration of the transmit periods in accordance with a power optimization protocol that results in minimizing power consumption by the ultrasound transducer.

2. The FSD of claim 1, wherein the control component adjusts the transmission power during the active mode based on a signal to noise (SNR) ratio of the reflected signals of the ultrasound signals.

3. The FSD of claim 2, wherein the control component incrementally decreases the transmission power during the active mode until the reflected signals of the ultrasound signals achieve a minimum SNR.

4. The FSD of claim 3, wherein the one or more fetal parameters comprise a heart rate of the fetus, and wherein the computer-executable components further comprise:
a signal processing component that determines values of the heart rate based on the reflected signals of the ultrasound signals, and wherein the control component incrementally decreases the transmission power based on the values satisfying acceptable fetal heart value criteria, and wherein the control component increases the transmission power based on one or more of the values failing to satisfy the acceptable fetal heart rate value criteria.

5. The FSD of claim 1, wherein the control component adjusts the duration of the transmit periods based on a depth of a heart of the fetus and/or a monitored signal to noise ratio (SNR) of the reflected signals of the ultrasound signals.

6. The FSD of claim 5, wherein the computer executable components further comprise:
a depth estimation component that estimates the depth of the heart based on the reflected signals of the ultrasound signals in association with adjusting the duration of the transmit periods by the control component and based on a change to the SNR observed in association with the adjusting, and wherein the control component sets the duration of the transmit periods based on the depth.

7. The FSD of claim 1, wherein the transmit periods are constrained by a first duration defined by a fixed start time and a fixed end time, wherein the duration of the transmit periods associated with the controlling comprises a second duration within the first duration corresponding to an active portion of the transmit periods, wherein the ultrasound transducer only transmits the ultrasound signals during the active portion, and wherein the controlling comprises adjusting the second duration of the active portion and/or a position of the active portion relative to the fixed start time and the fixed end time in accordance with the power optimization protocol.

8. The FSD of claim 7, wherein the control component adjusts the second duration of the active portion and/or the position of the active portion based on a depth of the heart of the fetus within the womb and/or a monitored signal to noise ratio (SNR) of the reflected signals of the ultrasound signals.

9. The FSD of claim 7, wherein the computer executable components further comprise:

a depth estimation component that estimates a depth of a heart of the fetus based on the reflected signals of the ultrasound signals in association with adjusting the second duration and/or the position of the active portion by the control component and based on a change to a signal-to-noise ratio (SNR) of the reflected signals of the ultrasound signals observed in association with the adjusting, and wherein the control component sets the second duration and/or the position of the active portion based on the depth.

10. The FSD of claim 7, wherein the control component monitors a signal-to-noise ratio (SNR) of the reflected signals of the ultrasound signals in association with adjusting the second duration and/or the position of the active portion, and wherein the computer executable components further comprise:

a depth estimation component that estimates and tracks changes to a depth of the heart of the fetus within the womb based in association with the adjusting.

11. The FSD of claim 1, wherein the control component monitors a signal-to-noise ratio (SNR) of the reflected signals of the ultrasound signals and decreases the duration of the transmit periods based on the SNR increasing or remaining the same or within a same range, and increases the duration of the transmit periods based on a decrease to the SNR.

12. The FSD of claim 1, wherein the ultrasound transducer operates in a sleep mode that comprises deactivation of transmission of the ultrasound signals, and wherein the control component controls switching operation of the ultrasound transducer between the sleep mode and the active mode based on a usage status of the FSD.

13. The FSD of claim 12, wherein the usage status of the FSD comprises an active usage status in which the FSD is positioned on the external body of the mother and an inactive usage status in which the FSD is not positioned on the external body of the mother, and wherein the computer executable components further comprise:

a usage status detection component that determines whether the usage status comprises the active usage status or the inactive usage status, and wherein the control component activates the active mode and deactivates the sleep mode based on the usage status being the active usage status and activates the sleep mode and deactivates the active mode based on the usage status being the inactive usage status.

14. The FSD of claim 13, wherein the usage status detection component determines whether the usage status comprises the active usage status or the inactive usage status based on monitored changes to an electrical impedance associated with the ultrasound transducer as determined based on monitored changes to a voltage level of the ultrasound signals transmitted.

15. A method, comprising:

controlling, by a fetal sensor device (FSD) comprising a processor, operations of an ultrasound transducer of the FSD in accordance with a power optimization protocol that results in minimizing power consumption by the FSD, wherein the ultrasound transducer is configured to measure signals representative of one or more fetal parameters of a fetus using doppler based ultrasound technology in association with positioning of the FSD on an external body of a mother of the fetus, wherein the FSD operates in an active mode that comprises alternating between transmit periods wherein the ultrasound transducer transmits ultrasound signals, and receive periods wherein the ultrasound transducer measures reflected signals of the ultrasound signals that are received by the ultrasound transducer during the receive periods, and wherein the controlling comprises controlling, while maintaining operation of the ultrasound transducer in the active mode, at least one of a transmission power of the ultrasound signals or a duration of the transmit periods in accordance with the power optimization protocol.

16. The method of claim 15, wherein the controlling comprises adjusting, by the FSD during the active mode, at least one of the transmission power or the duration of the transmit periods based on a signal-to noise ratio (SNR) of the reflected signals of the ultrasound signals.

17. The method of claim 16, wherein the one or more fetal parameters comprise a heart rate of the fetus, and wherein the adjusting comprises:

incrementally decreasing the transmission power during the active mode until the reflected signals of the ultrasound signals achieve a minimum SNR and based on respective values of the heart rate determined based on the reflected signals of the ultrasound signals corresponding to a valid fetal heart rate value; and increasing the transmission power during the active mode based on one or more of the respective values corresponding to an invalid fetal heart rate value.

18. The method of claim 15, wherein the controlling comprises adjusting, by the FSD, the duration of the transmit periods based on a depth of a heart of the fetus within the womb and/or a monitored signal to noise ratio (SNR) of the reflected signals of the ultrasound signals.

19. The method of claim 15, wherein the controlling comprises:

adjusting, by the FSD, the duration of the transmit periods based on a signal-to-noise ratio (SNR) of the reflected signals of the ultrasound signals;

estimating, by the FSD, a depth of a heart of the fetus based on a change to the SNR in association with the adjusting; and setting, by the FSD, the duration of the transmit periods based on the depth.

20. The method of claim 15, wherein the transmit periods are constrained by a first duration defined by a fixed start time and a fixed end time, wherein the duration of the transmit periods associated with the controlling comprises a second duration within the first duration corresponding to an active portion of the transmit periods, wherein the ultrasound transducer only transmits the ultrasound signals during the active portion, and wherein the controlling comprises adjusting the second duration of the active portion and/or a position of the active portion relative to the fixed start time and fixed the end time in accordance with the power optimization protocol.

21. The method of claim 20, wherein the adjusting comprises:

adjusting, by the FSD, the second duration and/or the position of the active portion;

monitoring, by the FSD, changes to a signal-to-noise ratio (SNR) of the reflected signals of the ultrasound signals in association with the adjusting; and setting, by the FSD, second duration and/or the position of the active portion to an optimal duration and/or optimal position based on the SNR of the reflected signals of the ultrasound signals received at the optimal duration and/or optimal position satisfying defined SNR optimization criteria.

22. The method of claim 20, further comprising:

estimating, by the FSD, a depth of a heart of the fetus based on the changes to the SNR in association with adjusting and/or based on previously correlated depth to the optimal duration and/or position.

23. The method of claim 15, wherein the FSD is further configured to operate in a sleep mode that comprises deactivation of transmission of the ultrasound signals by the ultrasound transducer, and wherein the controlling further comprises:

determining, by the FSD, whether a usage status of the FSD comprises an active usage status in which the FSD is placed on the external body of the mother or an inactive usage status in which the FSD is not placed on the external body of the mother; and controlling, by the FSD, switching operation of the FSD between the sleep mode and the active mode based on the usage status.

24. A non-transitory machine-readable storage medium, comprising executable instructions that, when executed by a processor of a fetal sensor device (FSD), facilitate performance of operations, comprising:

controlling operations of the FSD in accordance with a power optimization protocol that results in minimizing power consumption by the FSD, wherein the FSD comprises an ultrasound transducer configured to measure signals representative of one or more fetal parameters of a fetus using doppler based ultrasound technology in association with positioning of the FSD on an external body of a mother of the fetus, wherein the FSD operates in an active mode that comprises alternating between transmit periods wherein the ultrasound transducer transmits ultrasound signals, and receive periods wherein the ultrasound transducer measures reflected signals of the ultrasound signals that are received by the ultrasound transducer during the receive periods, and wherein the controlling comprises controlling, while maintaining operation of the ultrasound transducer in the active mode, at least one of a transmission power of the ultrasound signals or a duration of the transmit periods in accordance with the power optimization protocol.

* * * * *